(12) United States Patent
Forero Cortés et al.

(10) Patent No.: US 10,799,123 B2
(45) Date of Patent: Oct. 13, 2020

(54) ON-SITE DEVICE FOR DETECTING PRESENCE OF A LIQUID

(71) Applicants: Singapore University of Technology and Design, Singapore (SG); Changi General Hospital Pte Ltd, Singapore (SG)

(72) Inventors: Juan Pablo Forero Cortés, Singapore (SG); Suranga Chandima Nanayakkara, Singapore (SG); Shaohui Foong, Singapore (SG); Chang Yin Chionh, Singapore (SG)

(73) Assignees: Singapore University of Technology and Design, Singapore (SG); Changi General Hospital Pte Ltd, Singapore (SG)

( * ) Notice: Subject to any disclaimer, the term of this patent is extended or adjusted under 35 U.S.C. 154(b) by 520 days.

(21) Appl. No.: 15/743,937

(22) PCT Filed: Jul. 13, 2016

(86) PCT No.: PCT/SG2016/050327
§ 371 (c)(1),
(2) Date: Jan. 11, 2018

(87) PCT Pub. No.: WO2017/010942
PCT Pub. Date: Jan. 19, 2017

(65) Prior Publication Data
US 2018/0206739 A1 Jul. 26, 2018

(30) Foreign Application Priority Data
Jul. 14, 2015 (SG) .............................. 10201505521P

(51) Int. Cl.
*A61B 5/02* (2006.01)
*A61M 1/36* (2006.01)
(Continued)

(52) U.S. Cl.
CPC ............ *A61B 5/02042* (2013.01); *A61B 5/00* (2013.01); *A61M 1/3656* (2014.02);
(Continued)

(58) Field of Classification Search
CPC .............. A61B 5/1455; A61B 5/14551; A61B 5/14552; A61B 5/14532; A61B 5/02042;
(Continued)

(56) References Cited

U.S. PATENT DOCUMENTS 6,597,931 B1    7/2003  Cheng et al.
6,947,131 B2 *  9/2005  O'Mahony ......... A61M 1/1692
                                                    210/96.2
(Continued)

FOREIGN PATENT DOCUMENTS

DE          4014572 A1    11/1991
WO      WO2008/021462 A2   2/2008
WO      WO2013/186780 A1  12/2013

OTHER PUBLICATIONS

International Search Report corresponding to PCT/SG2016/050327, dated Oct. 20, 2016, five pages.
(Continued)

*Primary Examiner* — Chu Chuan Liu
(74) *Attorney, Agent, or Firm* — Kilpatrick Townsend & Stockton LLP

(57) ABSTRACT

An on-site device for detecting presence of a liquid from a site and a method for detecting presence of a liquid from a site using the on-site device, the device comprising a moisture detector arranged to detect the presence of the liquid based on one or more electrical characteristics of the liquid; a first optical detector assembly coupled to the moisture detector, the first optical detector assembly being configured to be activated upon detection of the presence of the liquid by the moisture detector; and wherein upon activation, the
(Continued)

first optical detector assembly is configured to detect a substance in the liquid based on one or more optical characteristics of the substance.

23 Claims, 23 Drawing Sheets

(51) Int. Cl.
*A61B 5/00* (2006.01)
*G01N 21/31* (2006.01)
*G01N 21/3554* (2014.01)

(52) U.S. Cl.
CPC ..... *G01N 21/3151* (2013.01); *G01N 21/3554* (2013.01); *A61B 2562/029* (2013.01); *A61B 2562/0214* (2013.01); *A61M 2205/15* (2013.01); *A61M 2205/3306* (2013.01); *G01N 2021/3155* (2013.01); *G01N 2021/3181* (2013.01); *G01N 2201/064* (2013.01)

(58) Field of Classification Search
CPC .............. A61B 5/0205; A61B 2562/00; A61B 2562/02; A61B 2562/0209; A61B 2562/0214; A61B 2562/0233; A61B 2562/0238; A61B 2562/029; A61B 2562/0295

See application file for complete search history.

(56) References Cited

U.S. PATENT DOCUMENTS

| 7,605,710 B2* | 10/2009 | Crnkovich ............. A61F 13/42 |
| | | 340/603 |
| 2006/0173253 A1 | 8/2006 | Ganapathy et al. |
| 2011/0184257 A1* | 7/2011 | Boll ..................... A61B 5/0059 |
| | | 600/306 |
| 2011/0237911 A1 | 9/2011 | Lamego et al. |
| 2013/0237812 A1 | 9/2013 | Warren et al. |

OTHER PUBLICATIONS

International Preliminary Report on Patentability corresponding to PCT/SG2016/050327 dated Aug. 31, 2017, six pages.
SG Application No. 11201800118T received a Supplemental Examination Report dated Mar. 3, 2018, 3 pages.

* cited by examiner

ON-SITE DEVICE FOR DETECTING PRESENCE OF A LIQUID

TECHNICAL FIELD

The present disclosure relates broadly to an on-site device for detecting presence of a liquid from a site and a method for detecting presence of a liquid from a site using an on-site device.

BACKGROUND

Undetected episodes of bleeding after procedures and surgery are of concern to the medical community. Examples of potential bleeding sites include areas where blood vessels (arteries or veins) have been punctured for access, or any trauma or surgical wound.

In particular, the risks associated with the use of venous lines and catheters are significantly higher. Central Venous Catheters (CVC) refers to prolonged vascular access devices for the administration of intravenous medication treatments, fluids, stem cell infusions, parenteral nutrition and haemodialysis among others. Main blood vessels such as subclavian (chest), jugular (neck) or femoral (groin) veins are typically accessed using such procedures. Bleeding can occur during catheter insertion, catheter in-dwelling period, and catheter removal.

In general, haemorrhages involve unacceptable exposure, not only because the blood loss significantly aggravates a patient's medical condition, but also because the stabilization and replacement of any ongoing treatment may incur a high price. In about 1% of cases, external and intense haemorrhages have been reported during the first number of hours after successful extraction of CVC. In such cases, a patient may lose as much as 250 mL to 500 mL of blood per minute. For such cases, prompt detection is crucial, and a proper control of the bleeding is mandatory.

Although protocols and policies to prevent the scenario may differ among different medical centres, it has been recognized that active medical supervision of the insertion site is required in order to restrain haemorrhages. To this end, typically, it is required that a medical personnel assess the insertion site for signs of bleeding e.g. an inspection every 15 minutes for 2 hours or every 30 minutes for 2 hours after the extraction of CVC.

However, such supervision protocols give rise to a number of problems. One problem is that routine inspection from medical personnel is required, thus resulting in inefficient use of manpower. Another problem is that, in between inspections, the insertion site is unsupervised for a considerable period of time in the context of haemorrhages. Intense bleeding episodes occurring during such periods of non-supervision can typically endanger a patient's life.

In addition to haemorrhages induced by venous needle dislodgement, the inventors have also recognized a desire to monitor or detect actively bleeding or blood loss prior to removal of the CVC, i.e. during the in-dwell period. Monitoring of other potential high risk bleeding sites also faces similar challenges.

Therefore, there is a need for an on-site device for detecting presence of a liquid from a site and a method for detecting presence of a liquid from a site using an on-site device that seek to address at least one of the above problems.

SUMMARY

In accordance with an aspect, there is provided an on-site device for detecting presence of a liquid from a site, the device comprising, a moisture detector arranged to detect the presence of the liquid based on one or more electrical characteristics of the liquid; a first optical detector assembly coupled to the moisture detector, the first optical detector assembly being configured to be activated upon detection of the presence of the liquid by the moisture detector; and wherein upon activation, the first optical detector assembly is configured to detect a substance in the liquid based on one or more optical characteristics of the substance.

The on-site device may comprise a sensor portion of the moisture detector disposed on a base surface of the on-site device for facing towards the site.

The on-site device may comprise the sensor portion of the moisture detector being configured to contact the site, and the moisture detector comprises a first electrode and a second electrode arranged to conduct electricity therebetween in the presence of the liquid.

The on-site device may comprise the sensor portion of the moisture detector being configured to detect a change in capacitance at the site due to the presence of the liquid at the site.

The first optical detector assembly may comprise a first electromagnetic wave emitting source and a first electromagnetic wave detector, the first electromagnetic wave emitting source being configured to emit electromagnetic waves with a wavelength of from about 470 nm to about 640 nm towards a surface of the site, and the first electromagnetic wave detector is configured to detect electromagnetic waves reflected from the surface of the site.

The first electromagnetic wave detector may be configured to detect the substance in the liquid based on an absorption by the substance of the electromagnetic waves.

The substance in the liquid may comprise haemoglobin.

The on-site device may further comprise a second optical detector assembly configured to detect the presence of the liquid based on one or more optical characteristics of the liquid, the second optical detector assembly comprising a second electromagnetic wave emitting source and a second electromagnetic wave detector, the second electromagnetic wave emitting source being configured to emit electromagnetic waves with a wavelength of from about 900 nm to about 1000 nm towards a surface of the site, and the second electromagnetic wave detector is configured to detect electromagnetic waves reflected from the surface of the site.

The on-site device may further comprise an alarm module coupled to the first optical detector assembly, the alarm module configured to trigger an alarm signal upon detection of the presence of the substance in the liquid by the first optical detector assembly.

The alarm signal may be arranged to activate an alarm of the on-site device, or the alarm signal is arranged to trigger an alert signal to be transmitted to a remote system via wireless transmission from the on-site device, or both.

The on-site device may further comprise a casing for housing components of the on-site device, the casing being capable of shielding the first optical detector assembly from external light sources.

The casing may be arranged to be sterilisable for re-use.

The site may comprise a catheter insertion site or a catheter removal site or a site where bleeding potentially occurs.

In accordance with another aspect, there is provided a method for detecting presence of a liquid from a site using an on-site device, the method comprising, detecting the presence of the liquid based on one or more electrical characteristics of the liquid using a moisture detector of the on-site device; activating a first optical detector assembly of the on-site device upon detection of the presence of the liquid by the moisture detector; and detecting a substance in the liquid based on one or more optical characteristics of the substance using the first optical detector assembly upon activation.

The method may further comprise contacting the site with a sensor portion of the moisture detector such that a first electrode and a second electrode of the moisture detector is capable of conducting electricity therebetween in the presence of the liquid.

The method may further comprise using a sensor portion of the moisture detector to detect a change in capacitance at the site due to the presence of the liquid at the site.

The step of detecting a substance in the liquid may comprise emitting electromagnetic waves with a wavelength of from about 470 nm to about 640 nm towards a surface of the site using a first electromagnetic wave emitting source of the first optical detector assembly, and using a first electromagnetic wave detector of the first optical detector assembly to detect electromagnetic waves reflected from the surface of the site.

The step of using the first electromagnetic wave detector of the first optical detector assembly to detect electromagnetic waves reflected from the surface of the site may comprise determining an absorption by the substance of the electromagnetic waves.

The substance in the liquid may comprise haemoglobin.

The method may further comprise detecting the presence of the liquid based on one or more optical characteristics of the liquid using a second optical detector assembly of the on-site device; emitting electromagnetic waves with a wavelength of from about 900 nm to about 1000 nm towards a surface of the site using a second electromagnetic wave emitting source of the second optical detector assembly; and using a second electromagnetic wave detector of the second optical detector assembly to detect electromagnetic waves reflected from the surface of the site.

The method may further comprise triggering an alarm signal upon detection of the presence of the substance in the liquid by the first optical detector assembly, the triggering using an alarm module coupled to the first optical detector assembly.

The method may further comprise activating an alarm of the on-site device using the alarm signal, or triggering an alert signal to be transmitted to a remote system via wireless transmission using the alarm signal, or both.

The method may further comprise shielding the first optical detector assembly from external light sources using a casing, the casing suitable for housing components of the on-site device.

The site may comprise a catheter insertion site or a catheter removal site or a site where bleeding potentially occurs.

In accordance with another aspect, there is provided a warning system for detecting presence of a liquid from one or more sites, the system comprising, one or more on-site devices as disclosed herein; an alarm monitoring remote system configured to receive one or more alert signals from the one or more on-site devices; wherein the alarm monitoring remote system is arranged to trigger an alarm to indicate the presence of liquid from the one or more sites.

The one or more alert signals may be configured to be transmitted to the alarm monitoring remote system by wireless transmission.

The alarm triggered at the alarm monitoring remote system may be further configured to be triggered at one or more personnel stations or at one or more alerting devices carried by personnel, or both.

In accordance with another aspect, there is provided a bandage for detecting presence of a liquid from a site, the bandage comprising, an on-site device as disclosed herein; a primary dressing capable of covering the site; a secondary dressing configured to cover the primary dressing and functioning as an external surface of the bandage; wherein the on-site device is provided between the primary dressing and the secondary dressing and is arranged to be positioned in the vicinity of the site with the primary dressing.

In accordance with another aspect, there is provided a non-transitory computer readable storage medium having stored thereon instructions for instructing a processing module of an on-site device for detecting presence of a liquid from a site to execute a method for detecting presence of a liquid from a site, the method comprising, detecting the presence of the liquid based on one or more electrical characteristics of the liquid using a moisture detector of the on-site device; activating a first optical detector assembly of the on-site device upon detection of the presence of the liquid by the moisture detector; and detecting a substance in the liquid based on one or more optical characteristics of the substance using the first optical detector assembly upon activation.

BRIEF DESCRIPTION OF THE DRAWINGS

Exemplary embodiments of the invention will be better understood and readily apparent to one of ordinary skill in the art from the following written description, by way of example only, and in conjunction with the drawings, in which.

DETAILED DESCRIPTION

Exemplary, non-limiting embodiments may provide an on-site device for detecting presence of a liquid from a site and a method for detecting presence of a liquid from a site using an on-site device.

Figure 1:
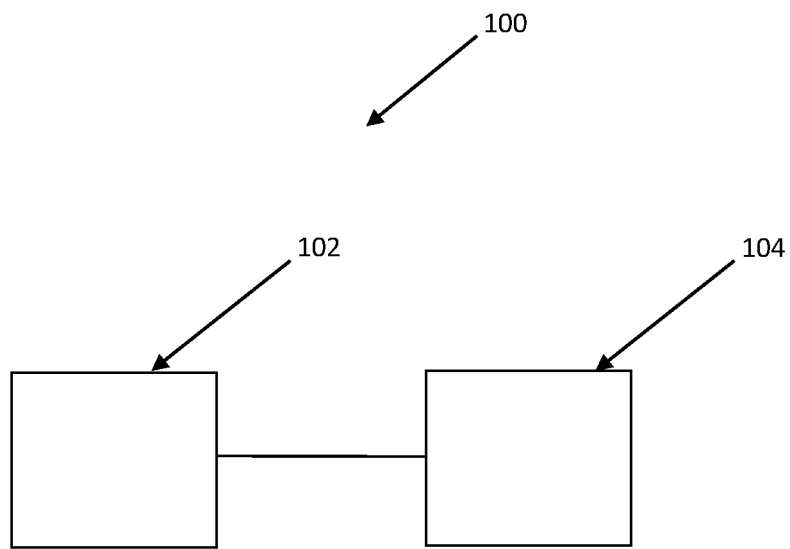
FIG. 1 is a schematic diagram of an on-site device for detecting presence of a liquid from a site in an exemplary embodiment.

FIG. 1 is a schematic diagram of an on-site device 100 for detecting presence of a liquid from a site in an exemplary embodiment. The on-site device 100 comprises a moisture detector 102 and a first optical detector assembly 104 coupled to the moisture detector 102. The moisture detector 102 is arranged to detect the presence of the liquid based on one or more electrical characteristics of the liquid. The first optical detector assembly 104 is configured to be activated upon detection of the presence of the liquid by the moisture detector 102. Upon activation, the first optical detector assembly 104 is configured to detect a substance in the liquid based on one or more optical characteristics of the substance.

In the exemplary embodiment, the on-site device 100 may further comprise a second optical detector assembly (not shown). The second optical detector assembly is configured to detect the presence of the liquid based on one or more optical characteristics of the liquid.

In the exemplary embodiment, the on-site device 100 may further comprise an alarm module (not shown) coupled to the first optical detector assembly 104. The alarm module is configured to trigger an alarm signal upon detection of the presence of the substance in the liquid by the first optical detector assembly 104. The alarm signal may activate an alarm of the on-site device 100. Alternatively or in addition, the alarm signal may trigger an alert signal to be transmitted via wireless transmission (e.g. by Bluetooth technology) from the on-site device 100 to a remote system such as an alarm monitoring remote system (not shown).

In the exemplary embodiment, the on-site device 100 may further comprise a casing (not shown) for housing components of the on-site device 100, such as the first optical detector assembly 104 and the moisture detector 102. The casing is capable of shielding the first optical detector assembly 104 from external light sources. The casing may also be arranged such that the casing may be sterilised for re-use.

Figure 20:
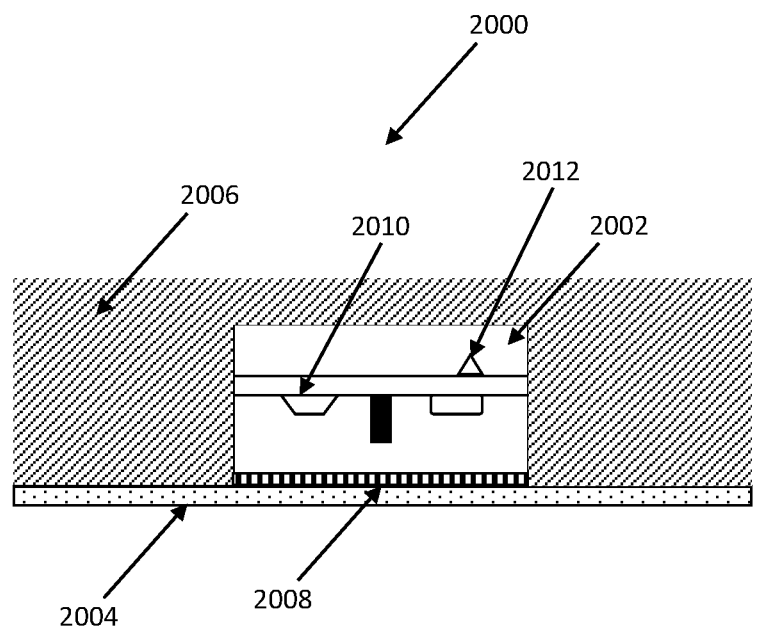
FIG. 20 is a schematic cross sectional view drawing of an integrated bandage in an exemplary embodiment.

FIG. 20 is a schematic cross sectional view drawing of an integrated bandage 2000 in an exemplary embodiment. The integrated bandage 2000 is configured for application at a site where presence of liquid e.g. blood is to be monitored. The integrated bandage 2000 comprises an on-site device 2002 positioned in an enclosure between a primary dressing 2004 and a secondary dressing 2006. The primary dressing 2004 is a gauze/bandage dressing which is configured to contact and protect the site. The secondary dressing 2006 is a bandage dressing which covers and protects the primary dressing 2004. When the bandage 2000 is placed over the site and the primary dressing 2004 contacts the site, the secondary dressing 2006 functions as an external surface of the integrated bandage 2000.

In the exemplary embodiment, the on-site device 2002 comprises a moisture detector 2008 and a first optical detector assembly 2010 coupled to the moisture detector 2008. The on-site device 2002, moisture detector 2008 and first optical detector assembly 2010 function substantially similarly to the on-site device 100, moisture detector 102 and first optical detector assembly 104 of FIG. 1 respectively. The moisture detector 2008 is configured to detect presence of moisture based on a capacitive sensing technique. The on-site device 2002 further comprises an on-board alarm module 2012 which is configured to produce a sound-based alarm, a battery unit (not shown) which allows the on-site device 2002 to operate for at least 6 hours, and a processing unit such as a micro-controller (not shown) which controls and operates the components of the on-site device 2002.

In the exemplary embodiment, the integrated bandage 2000 is configured such that the on-site device 2002 is provided between the primary dressing 2004 and the secondary dressing 2006 and is arranged to be positioned in close proximity to the site where presence of liquid is to be monitored, e.g. in the vicinity of or on top of the site with the primary dressing 2004. The primary dressing 2004, secondary dressing 2006, or both are made of absorbent material to absorb liquid e.g. blood from the site.

In the exemplary embodiment, the integrated bandage 2000 is sterilisable and is configured as a disposable single use bandage. In addition, the on-site device 2002 may be housed in a casing or a structured implement to hold/secure the components of the on-site device 2002.

In the exemplary embodiment, the thickness profile of the on-site device 2002 may be reduced/flattened by reducing the thickness of the respective components of the on-site device 2002; and/or rearranging the components of the on-site device 2002 such that the components are laid adjacent to each other in substantially the same plane. For example, the battery unit and the first optical detector assembly 2010 may be positioned adjacent to each other in substantially the same plane to achieve a relatively flatter thickness profile for the on-site device 2002.

Figure 2A:
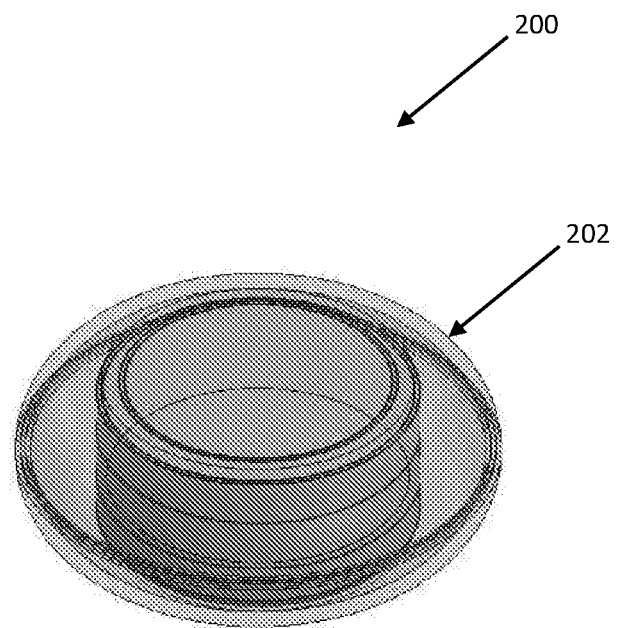
FIG. 2A is a schematic perspective view drawing of an on-site device for detecting presence of a liquid from a site in an exemplary embodiment.

FIG. 2A is a schematic perspective view drawing of an on-site device 200 for detecting presence of a liquid from a site in an exemplary embodiment. The on-site device comprises a casing 202 having a disc shape, with a diameter of about 4 cm and a height of about 1.7 cm. The on-site device 200 is a standalone device and is configured to be portable. The weight of the on-site device 200, including the casing 202, is about 52.4 g.

Figure 2B:
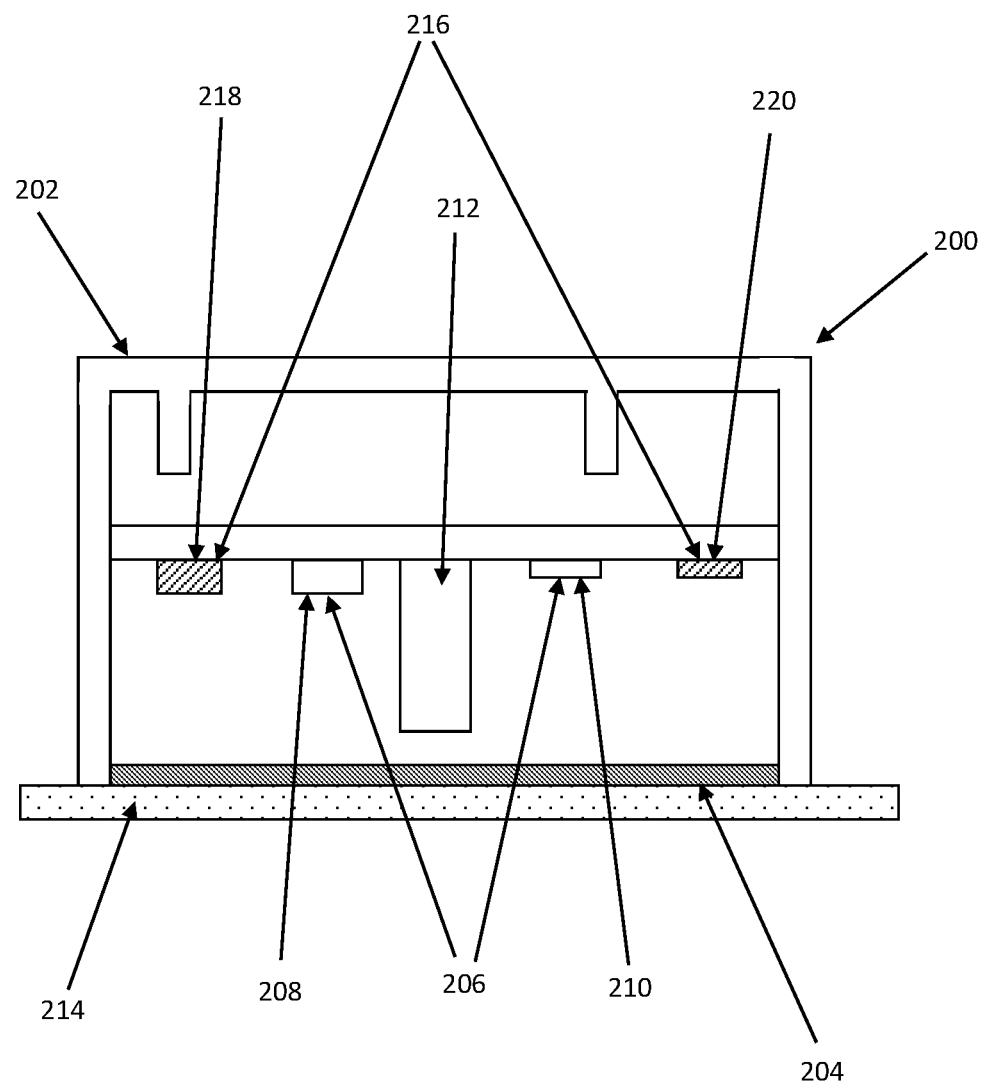
FIG. 2B is a schematic cross sectional view drawing of the on-site device in FIG. 2A.

FIG. 2B is a schematic cross sectional view drawing of the on-site device 200 in FIG. 2A. The on-site device 200 further comprises a moisture detector 204 configured to detect presence of a liquid based on one or more electrical characteristics of the liquid and a first optical detector assembly 206 configured to detect a substance in the liquid based on one or more optical characteristics of the substance. In the exemplary embodiment, the substance is haemoglobin.

The on-site device 200 is disposed or positioned on a site surface 214 such as an intrusion site, an infusion site, an invasive site, a catheter insertion site, a catheter removal site, trauma wound, surgical wound etc.

In the exemplary embodiment, the moisture detector 204, or at least a sensor portion of the moisture detector 204, is positioned at a base surface of the on-site device 200 and is configured to detect for presence of the liquid via a contact sensing mechanism based on the electrical conductivity (or resistivity) of the liquid. The base surface is for facing towards the site surface 214.

In general, the types of liquid which can be detected by the moisture detector 204 are electrically conductive and include water, ionic chemical solutions/mixtures, and body fluids such as blood, serum and urine.

In other exemplary embodiments, the moisture detector 204, or at least a sensor portion of the moisture detector 204, may be configured to detect presence of the liquid via a capacitive sensing mechanism based on a change in capacitance over the surface 214 or at the site due to the presence of the liquid at the site.

In the exemplary embodiment, the first optical detector assembly 206 is configured to be activated upon detection of the presence of liquid by the moisture detector 204. The first optical detector assembly 206 is positioned within the casing 202 of the on-site device 200 and comprises a first electromagnetic (EM) wave emitter 208 e.g. a Red-Blue-Green (RGB) light emitting diode (LED) emitter and a first electromagnetic (EM) wave detector 210 e.g. a colour sensor tuned to detect one of the RGB light. The casing 202 functions to house/protect and shield/isolate the electronic components of the first optical detector assembly 206 and prevents external light sources from interfering with the first EM wave detector 210 of the first optical detector assembly 206. Upon activation, the first optical detector assembly 206 is configured to detect for presence of haemoglobin in the liquid based on an optical absorption characteristic of haemoglobin. The presence of haemoglobin in the liquid indicates that the liquid detected by the moisture detector 204 is blood.

In the exemplary embodiment, the first EM wave emitter 208 and the first EM wave detector 210 of the first optical detector assembly 206 are positioned at opposite ends of the on-site device 200 and are separated by a partition wall 212. The partition wall 212 functions to prevent electromagnetic waves emitted by the first EM wave emitter 208 from directly reaching the first EM wave detector 210. In order to detect for presence of haemoglobin upon activation, the first EM wave emitter 208 is configured to emit light having a predetermined wavelength from about 470 nm to about 640 nm (e.g. green, yellow or orange light of the visible colour spectrum), and preferably about 528 nm (green light) towards the surface 214 of the site e.g. a surface of a bandage dressing covering a catheter removal site. The first EM wave detector 210 is configured to detect presence of reflected EM waves, in particular light having a wavelength from about 520 nm to about 580 nm reflected from the surface 214 of the site. To allow light emitted from the first EM wave emitter 208 to reach the surface 214 of the site, the base surface of the on-site device 200 is made from a material which is substantially transparent to EM waves.

The first optical detector assembly 206 determines the presence of haemoglobin in a liquid based on a level of light at the predetermined wavelength detected by the first EM wave detector 210. The first EM wave detector 210 is configured to trigger a signal once the level of light detected by the first EM wave detector 210 falls below a predetermined threshold level. If the liquid detected by the moisture detector 204 does not contain haemoglobin, light emitted by the first EM wave emitter 208 is reflected from the surface 214 of the site and reaches the first EM wave detector 210. The level of light detected by the first EM wave detector 210 thus is above the pre-determined threshold level and no signal is triggered. If the liquid detected by the moisture detector 204 contains haemoglobin, light of the predetermined wavelength emitted by the first EM wave emitter 208 is absorbed by the haemoglobin present in the liquid. As a result, the level of light reflected from the surface 214 of the site and the level of light detected by the first EM wave detector 210 decreases. The level of light detected by the first EM wave detector 210 is inversely proportional to the amount of haemoglobin present in the liquid. In the exemplary embodiment, once the level of light detected by the first EM wave detector 210 falls below the pre-determined threshold level, a signal is triggered by the first EM wave detector 210 to indicate the presence of haemoglobin, thus indicating that the liquid detected by the moisture detector 204 is blood. Therefore, in the exemplary embodiment, the detection of the substance in the liquid is based on an absorption by the substance of the EM waves.

In the exemplary embodiment, a second optical detector assembly 216 may be provided. The second optical detector assembly 216 comprises a second EM wave emitter 218 e.g. an infrared (IR) LED emitter and a second EM wave detector 220 e.g. a photodiode. The second optical detector assembly 216 is configured to detect presence of a liquid based on one or more optical characteristics of the liquid e.g. absorption characteristics of EM waves of an aqueous liquid/solution. The second optical assembly 216 is configured to detect a liquid which is capable of absorbing EM waves having a wavelength of from about 900 nm to about 1000 nm, e.g. infrared waves.

The second EM wave emitter 218 of the second optical detector assembly 216 is configured to emit EM waves having a wavelength from about 900 nm to about 1000 nm towards the surface 214 of the site. The second EM wave detector 220 is configured to detect presence of reflected EM waves, in particular infrared waves having a wavelength from about 900 nm to about 1000 nm reflected from the surface 214 of the site. The second optical detector assembly 216 is configured to detect for presence of liquid by emitting EM waves at pre-determined time intervals. If liquid is present, the liquid absorbs the EM waves emitted by the second EM wave emitter 218, and a level of the EM wave detected by the second EM wave detector 220 decreases. A decrease in the EM wave detected by the second EM wave detector 220 triggers a signal, indicating the presence of the liquid.

In the exemplary embodiment, the second optical detector assembly 216 is complementary to the moisture detector 204 for detecting the presence of the liquid.

In the following figures (FIG. 3A to FIG. 7), exemplary embodiments of a moisture detector for detecting presence of a liquid based on one or more electrical characteristics of the liquid are described. The moisture detectors in the following exemplary embodiments function substantially similarly to the moisture detector 102 of FIG. 1 and the moisture detector 204 of FIG. 2B. The moisture detectors may be configured to detect presence of moisture using either a contact sensing technique or a capacitive sensing technique.

Figure 3A:
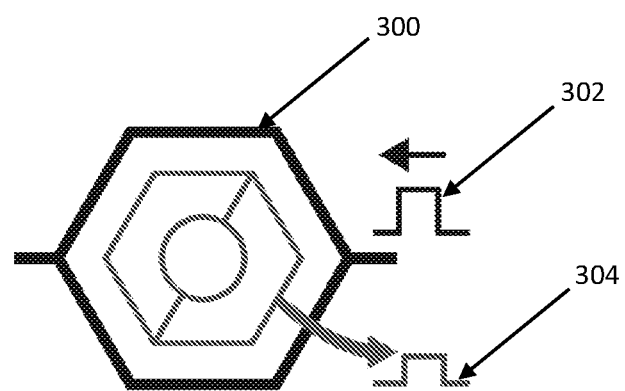
FIG. 3A is a schematic circuit layout of an electric resistive pattern in an exemplary embodiment.

FIG. 3A is a schematic circuit layout of an electric resistive pattern 300 in an exemplary embodiment. The electric resistive pattern 300 is based on a contact sensing approach to detect presence of a liquid based on an electrical conductivity characteristic of the liquid. The electric resistive pattern 300 functions as a sensor portion of the moisture detector and comprises two electrodes with a first electrode 302 configured to transmit electric pulses and a second electrode 304 which is passive and which is configured to receive electric pulses from the first electrode 302 in contact via a conductive medium such as a liquid. Thus, in the presence of the liquid, the first electrode 302 and the second electrode 304 are arranged to conduct electricity therebetween the two electrodes 302, 304.

Figure 3B:
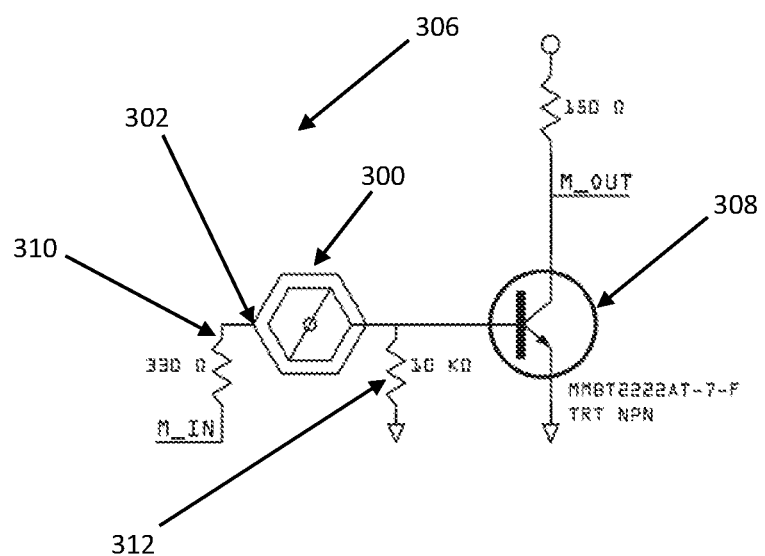
FIG. 3B is a schematic circuit diagram of a moisture detector in the exemplary embodiment.

FIG. 3B is a schematic circuit diagram of a moisture detector 306 in the exemplary embodiment. The moisture detector 306 functions substantially similarly to the moisture detector 102 of FIG. 1 and the moisture detector 204 of FIG. 2B. The moisture detector 306 is configured to detect presence of a liquid based on a resistive sensing technique. The moisture detector 306 comprises an electric resistive pattern 300 which is sensitive to the presence of conductive liquids as a sensor portion. The moisture detector 306 is configured to send an electric pulse having a duration of about milliseconds at a frequency of 10 Hz via the first electrode 302. A transistor 308 is provided to amplify the signal that is being sent. A resistor 310 having a resistance of 330Ω is provided to limit the maximum current that can be drained from the pin of a microprocessor (not shown). The maximum current that can be drained is about 10 mA, in cases where the pads of the electric resistive pattern 300 are short-circuited. A high impedance resistor 312 having a resistance of 10 kΩ is placed in the base of the transistor 308 to fix the voltage and avoid a floating pin. The transistor 308 is configured to amplify the signal so that the ADC (analogue to digital) converter of the microprocessor has a significantly amplified signal to work with.

The moisture detector 306 is configured to detect $H_2O$ or water, which typically has an electrical resistivity of approximately 2KΩ per cm and is the least conductive substance that the moisture detector 306 is configured to detect. In the exemplary embodiment, the distance between the pads of the electric resistive pattern 300 is reduced and set at about 0.25 mm to minimize the losses caused by the medium between the first electrode 302 and the second electrode 304. In the presence of a conductive/ionic liquid, the resistance of the liquid medium decreases, allowing electricity to flow from the first electrode 302 to the second electrode 304, or therebetween the two electrodes 302, 304. If the current through the second electrode 304 is above a predetermined threshold level, a signal is triggered by the moisture detector 306 to indicate the presence of a liquid. The signal is configured to activate an optical detector assembly which functions substantially similarly to the first optical detector assembly 104 of FIG. 1 and the first optical assembly 206 of FIG. 2B, for detecting the presence of a substance in the liquid.

In general, blood has an average electrical conductivity of from about 0.61 S/m to about 0.70 S/m. Urine has an average electrical conductivity of from about 0.11 S/m to about 0.39 S/m. Water or $H_2O$ has an average electrical conductivity of from about 0.0005 S/m to about 0.05 S/m. Therefore, it has been recognised by the inventors that a threshold level which is sufficiently sensitive to detect the presence of water is effectively capable of detecting other liquids such as blood, serum or urine, which have higher electrical conductivities as compared to water. Depending on the pattern of the electric resistive pattern 300, the sensitivity of the moisture detector 300 can also be varied.

Figure 4:
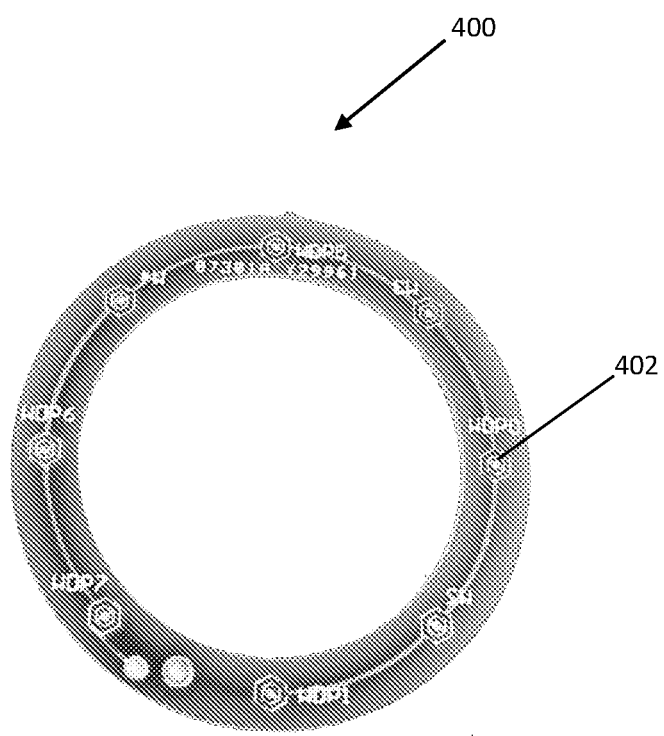
FIG. 4 is a schematic diagram of a printed circuit board (PCB) for a moisture detector for an exemplary implementation.

FIG. 4 is a schematic diagram of a printed circuit board (PCB) 400 for a moisture detector for an exemplary implementation. The PCB 400 comprises one or more electrical contacts e.g. 402 for contacting liquid. In the exemplary implementation, the PCB 400 is capable of detecting the presence of a liquid based on a contact or resistive sensing technique.

Figure 5A:
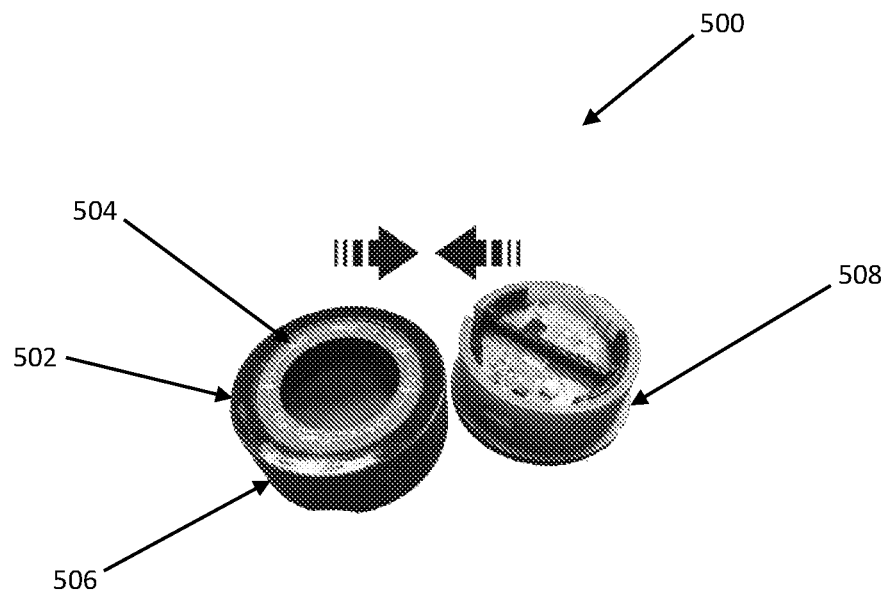
FIG. 5A is a picture showing a perspective view of an on-site device for detecting presence of a liquid from a site in an exemplary embodiment.
Figure 5B:
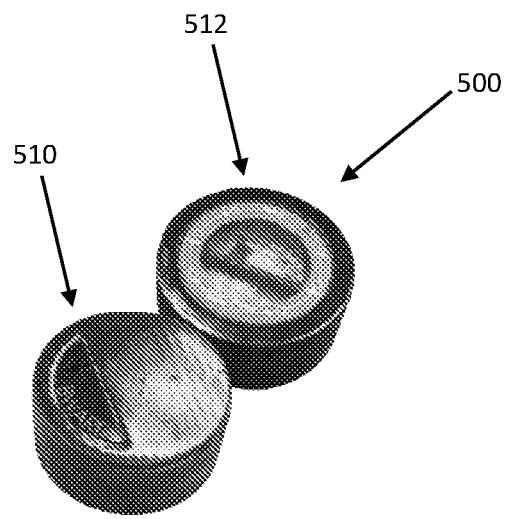
FIG. 5B is a picture showing another perspective view of the on-site device of FIG. 5A.

FIG. 5A is a picture showing a perspective view of an on-site device 500 for detecting presence of a liquid from a site in an exemplary embodiment. FIG. 5B is a picture showing another perspective view of the on-site device 500 of FIG. 5A. As shown, the on-site device 500 comprises a casing 502 and a moisture detector 504 disposed on a surface of the casing 502. In the exemplary embodiment, the moisture detector is configured to detect presence of a liquid using contact sensing, based on one or more electrical characteristics of the liquid. The on-site device 500 may be applied to a surface of a site e.g. a bandage dressing covering a catheter removal site such that the moisture detector 504 contacts the surface of the bandage dressing and is capable of detecting the presence of liquid at the surface of the bandage dressing.

In the exemplary embodiment, the casing 502 comprises a first shell 506 and a second shell 508 arranged to be assembled in a complementary manner. In FIG. 5A, the first shell 506 and the second shell 508 are separated from each other. In FIG. 5B, the first shell 506 and the second shell 508 are assembled together to form the on-site device 500. FIG. 5B shows the on-site device 500 in a top view 510 and a bottom view 512. As shown, the moisture detector 504 is circular in shape and is disposed parallel to a circular circumference of the casing 502. The moisture detector 504 is disposed on a base surface of the casing 502 for facing towards a site for monitoring.

Figure 6:
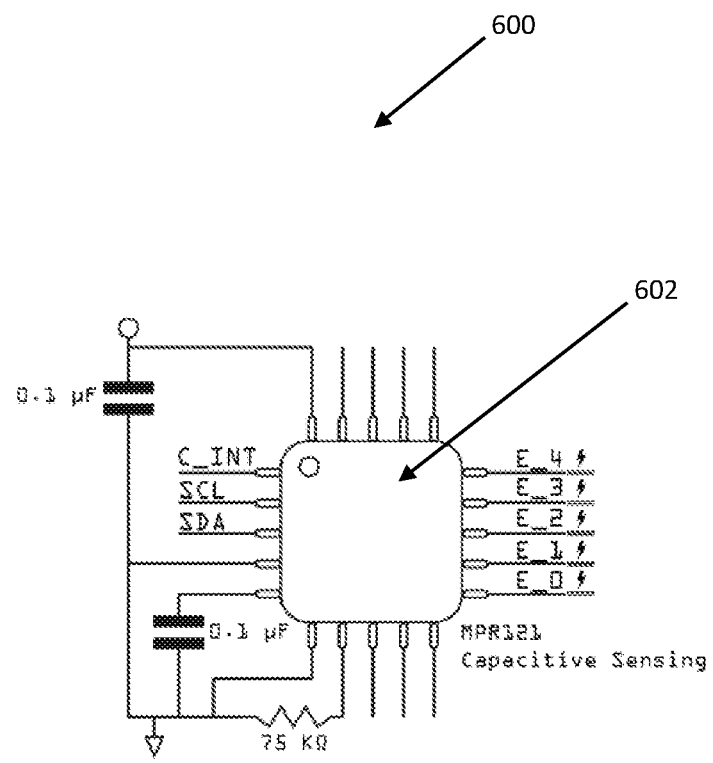
FIG. 6 is a schematic circuit diagram of a moisture detector in another exemplary embodiment.

FIG. 6 is a schematic circuit diagram of a moisture detector 600 in another exemplary embodiment. The moisture detector 600 functions similarly to the moisture detector 102 of FIG. 1 and is configured to detect presence of a liquid based on a capacitive sensing technique.

In the exemplary embodiment, the moisture detector 600 comprises a MPR121 capacitive touch sensor controller 602 driven by an I2C interface. The MPR121 capacitive touch sensor controller 602 is installed into an application circuit using 0.1 uF capacitors for input power noise rejection. SCL and SDA are the I2C serial clock and data pins respectively. The C_INT pin is used as an interrupt to inform the system that a change in the electrode readings has occurred.

The moisture detector 600 is configured for use in an on-site device for detecting presence of a liquid from a site and is capable of detecting changes in the capacitance at the site using electrodes placed at the base of the on-site device. The electrodes function as a sensor portion of the moisture detector 600. The electrodes are configured to be positioned behind a film cover (not shown) made of plastic, acrylic or glass film at the base of the on-site device. That is, the film cover is exposed to the exterior of the on-site device, and faces towards the site. In the exemplary embodiment, the sensitivity of the moisture detector 600 is configured to enable detection of the presence of liquid through the film cover. The thickness of the film cover may be up to 1 mm. The moisture detector 600 has relatively low energy consumption, typically consuming about 29 μA at a sampling frequency of 62.5 Hz.

In operation, the MPR121 capacitive touch sensor controller 602 monitors a set of electrodes for changes in capacitance. In presence of moisture/water, capacitance as measured by the electrodes changes. Once a pre-determined threshold is reached, the MPR121 capacitive touch sensor controller 602 informs a main controller e.g. a microcontroller via the C_INT pin and raw information (raw values from each electrode) is transmitted via I2C using the SCL and SDA pins.

Figure 7:
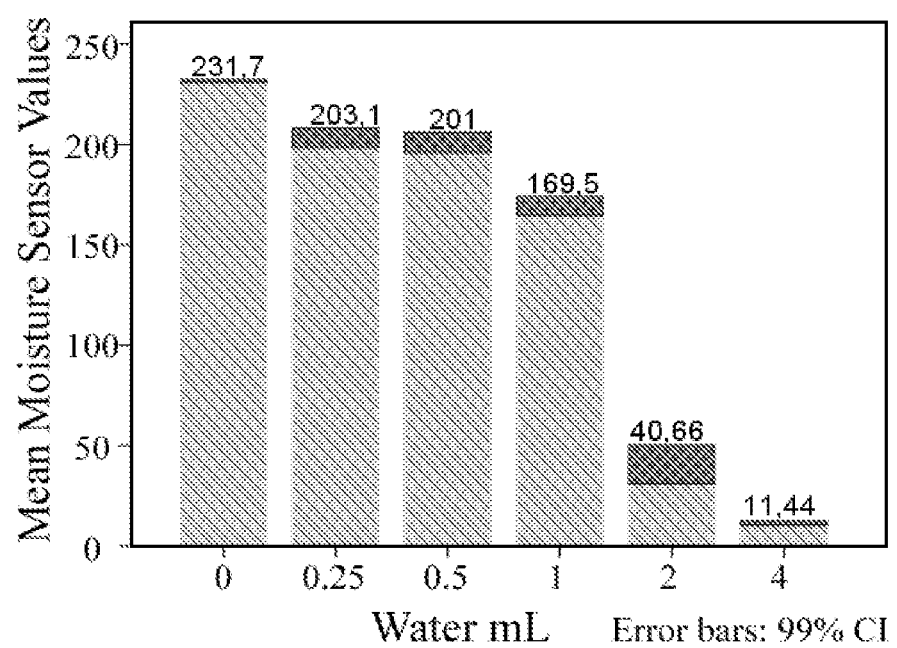
FIG. 7 is a bar chart showing the effects of liquid volume on the sensitivity of a moisture detector in an exemplary embodiment using the resistive sensing technique.

FIG. 7 is a bar chart showing the effects of liquid volume on the sensitivity of a moisture detector in an exemplary embodiment using the resistive sensing technique. Based on experimental data, it is demonstrated that the moisture detector can be triggered by the liquid volumes under test with a minimum mean difference of 28.56 (SE=2.794, $p<0.01$). The minimum mean difference is specifically the difference in sensor values between 0 ml of water and 0.25 ml of water. Thus, the moisture detector may be configured to be triggered at different levels of humidity by adjusting a threshold level of the moisture sensor values. For example, the threshold level may be set to 200 (this threshold value corresponds to the range of values which an on board controller 8-bit input port is capable of reading, i.e. from 0 to 255) such that a minimum volume of about 0.25 ml of liquid is able to trigger the moisture detector, thus indicating the presence of the liquid.

In the following figures (FIG. 8A to FIG. 10B), exemplary embodiments of a first optical detector assembly for detecting a substance in a liquid based on one or more optical characteristics of the substance are described. The first optical detector assemblies in the following exemplary embodiments function substantially similarly to the first optical detector assembly 104 of FIG. 1 and the first optical detector assembly 206 of FIG. 2B and are configured to be activated upon detection of the presence of a liquid by a moisture detector.

Figures 8A, 8B, 8C:
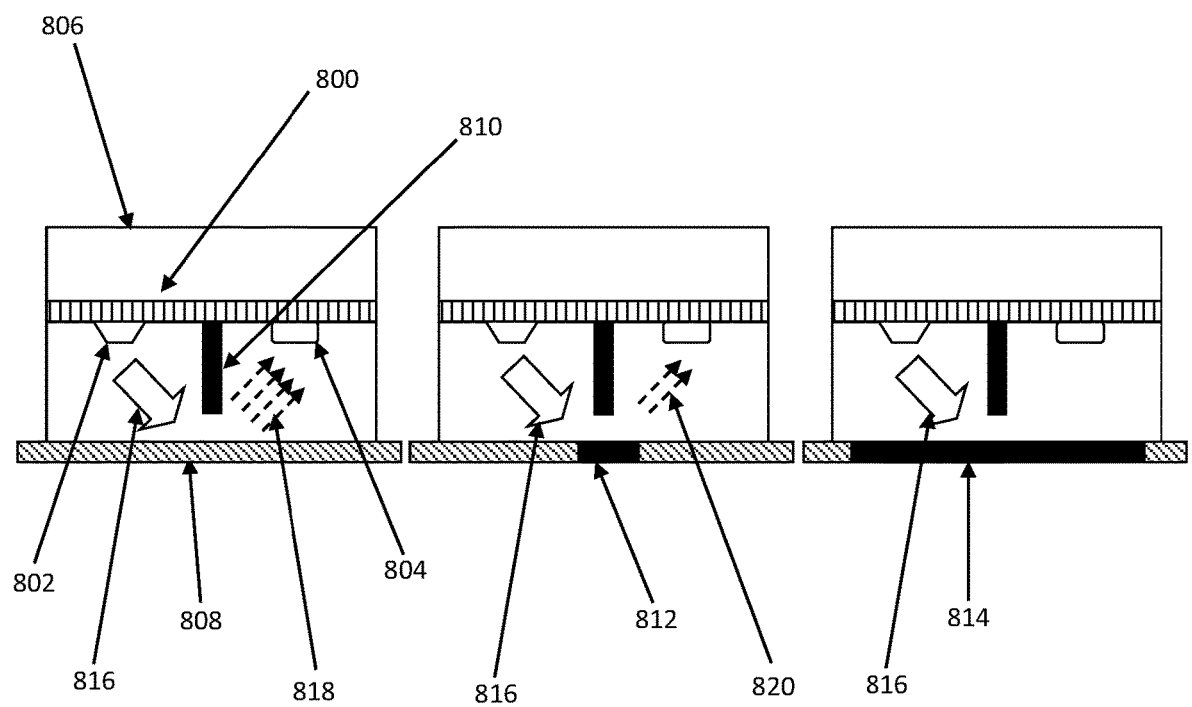
FIGS. 8A-8C show schematic diagrams of a first optical detector assembly in a cross-sectional view in an exemplary embodiment.

FIGS. 8A to 8C show schematic diagrams of a first optical detector assembly 800 in a cross-sectional view in an exemplary embodiment. The first optical detector assembly 800 is configured to be activated upon detecting the presence of a liquid. Upon activation, the first optical detector assembly 800 is configured to detect a substance in the liquid based on one or more optical characteristics of the substance. In the exemplary embodiment, the first optical detector assembly 800 is configured to detect the presence of haemoglobin based on the optical absorption characteristics of haemoglobin. Presence of haemoglobin is an indication that the liquid detected is blood.

The first optical detector assembly 800 comprises a first EM wave emitter 802 e.g. a RGB emitter and a first EM wave detector 804 e.g. a colour sensor, and the first optical detector assembly 800 is positioned inside a casing 806. The casing 806 comprises a base surface 808 which is substantially transparent to EM waves. The remaining surfaces of the casing 806 are substantially opaque to EM waves to prevent external light sources from interfering with the electronic sensors and circuitry such as the first EM wave emitter 802 and the first EM wave detector 804 of the first optical detector assembly 800. The first EM wave emitter 802 and the first EM wave detector 804 are separated from each other by a partition wall 810 to minimize the occurrence of EM waves from the first EM wave emitter 802 directly reaching the first EM wave detector 804. The first EM wave emitter 802 and the first EM wave detector 804 are arranged to face towards the base surface 808 which is contacted with or in proximity to a surface of a site e.g. surface of a bandage dressing covering a catheter removal site.

In the exemplary embodiment, the first EM wave emitter 802 is a RGB LED emitter (e.g. model no. LRTBGFTG T7AW) configured to emit light with wavelengths centred at about 470 nm (blue), about 528 nm (green) and about 625 nm (red). The first EM wave detector 804 is a colour sensor (e.g. model no. TCS3414FN) configured to detect light with wavelengths centred at about 470 nm, about 524 nm and about 640 nm. The first EM wave emitter 802 may be configured to emit EM waves in a continuous manner or in pulses of light.

In order to detect the presence of haemoglobin, the first EM wave emitter 802 is configured to emit EM waves towards the surface of the bandage dressing and the first EM wave detector 804 is configured to detect EM waves reflected from the surface of the bandage dressing. The detection of haemoglobin is based on a predetermined threshold level of EM waves detected by the first EM wave detector 804. An increase in the concentration of haemoglobin at the surface of the bandage dressing results in an increase in the amount of EM waves (e.g. EM waves having a wavelength of about 528 nm) being absorbed by the haemoglobin. Consequently, the amount of EM waves reflected from the surface of the bandage dressing and detected by the first EM wave detector 804 decreases. Once the level of EM wave detected by the first EM wave detector 804 falls below a predetermined threshold level, a signal is triggered by the first EM wave detector 804 to indicate the presence of haemoglobin in the liquid detected on the surface of the bandage dressing. The strength of the signal triggered by the first EM wave detector 804 changes according to the level of haemoglobin detected. For example, strength of the triggered signal may increase with increasing levels of haemoglobin detected by the first EM wave detector 804.

In FIG. 8A, upon activation and in the absence of haemoglobin in the liquid, EM waves emitted (as indicated by arrow 816) from the first EM wave emitter 802 are reflected (as indicated by reference numeral 818) from the surface of the bandage dressing such that the level of EM waves detected by the first EM wave detector 804 is above the predetermined threshold level. No signal is triggered as haemoglobin is not detected to be present.

In FIG. 8B, a first quantity of blood 812 is present on the surface of the bandage dressing. The first quantity of blood 812 covers part of the base surface 808 of the casing 806. Upon activation, a portion of the EM waves emitted (as indicated by arrow 816) by the first EM wave emitter 802 is absorbed by haemoglobin present in the first quantity of blood 812, resulting in a decrease in the level of light being reflected (as indicated by reference numeral 820 with fewer and less dense arrows) from the surface of the bandage dressing and detected by the first EM wave detector 804.

In FIG. 8C, a second quantity of blood 814 is present on the surface of the bandage dressing. The second quantity of blood 814 is higher as compared to the first quantity of blood 812 and covers substantially the entire base surface 808 of the casing 806. Upon activation, the EM wave emitted (as indicated by arrow 816) by the first EM wave emitter 802 is completely absorbed by the haemoglobin present in the second quantity of blood 814, such that the first EM wave detector 804 ceases to detect EM waves reflected from the surface of the bandage dressing. A signal is triggered by the optical detector assembly 800 to confirm the presence of haemoglobin in blood.

Figure 9A:
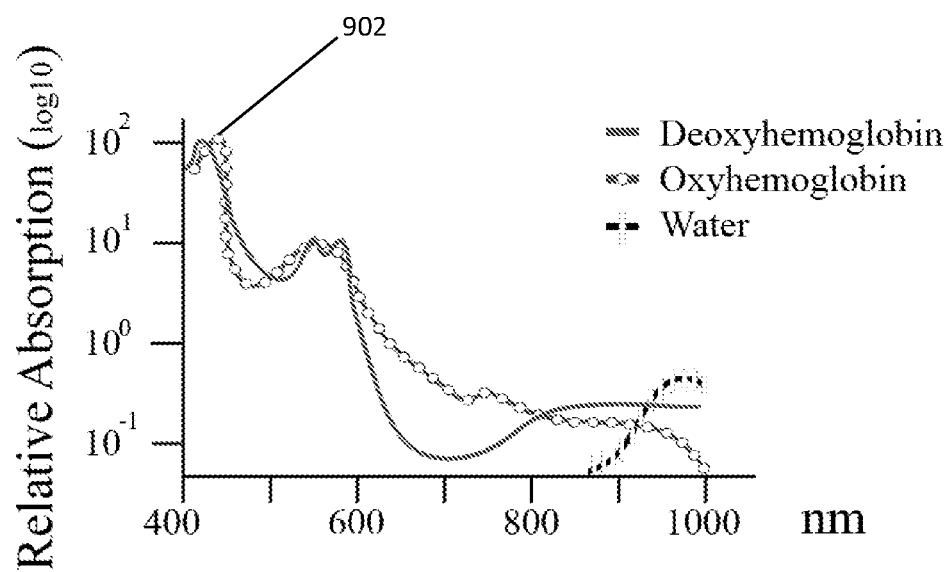
FIG. 9A is a graph showing a comparison of relative absorption between deoxyhaemoglobin, oxy-haemoglobin and water.
Figure 9B:
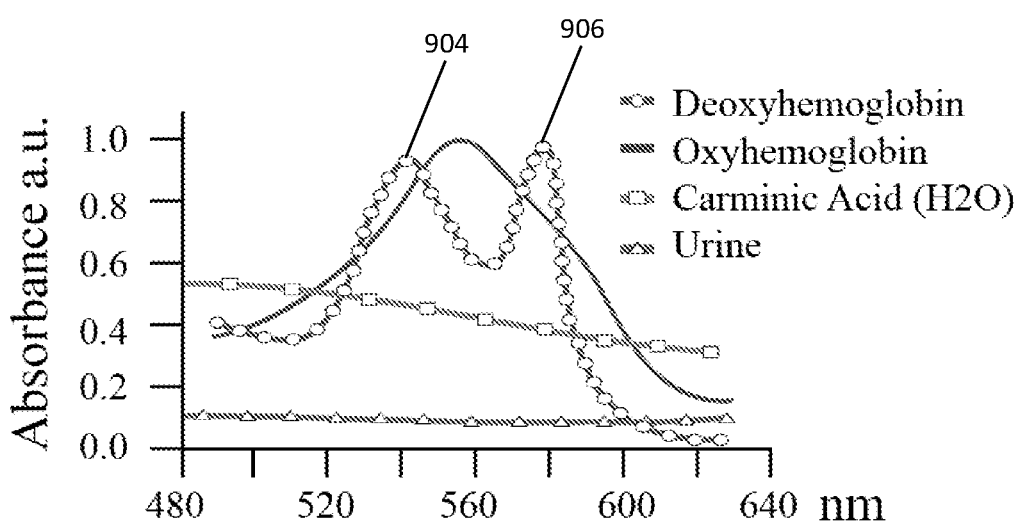
FIG. 9B is a graph showing a comparison of absorbance between deoxyhaemoglobin, oxy-haemoglobin, carminic acid and urine.

FIG. 9A is a graph showing a comparison of relative absorption between deoxyhaemoglobin, oxy-haemoglobin and water. FIG. 9B is a graph showing a comparison of absorbance between deoxyhaemoglobin, oxy-haemoglobin, carminic acid and urine.

As shown in FIG. 9A and FIG. 9B, different substances exhibit different absorption spectra. It has been recognised by the inventors that every known substance exhibits a specific spectral response. The use of an optical detector assembly in detecting presence of a substance in a liquid is based on the optical absorption properties of haemoglobin, a biomolecule found in red blood cells. Haemoglobin is responsible for carrying oxygen in the bloodstream.

In order to clearly differentiate haemoglobin from other substances that may lead to a false positive, an optimal range of light wavelengths is considered. By using an appropriate range of wavelengths, haemoglobin shows significantly higher levels of absorption as compared to other substances, or vice versa.

As shown in FIG. 9A and FIG. 9B, haemoglobin has a maximum light absorption window between 520 and 580 nm. Compare peaks 902, 904, 906. On the contrary, both water and urine have relatively lower absorption levels between 520 nm and 580 nm, thus creating a significant contrast with haemoglobin. Therefore, an appropriate range of wavelengths which is suitable for differentiating haemoglobin from other substances has been chosen from about 470 nm to about 640 nm, preferably about 528 nm.

Figure 9C:
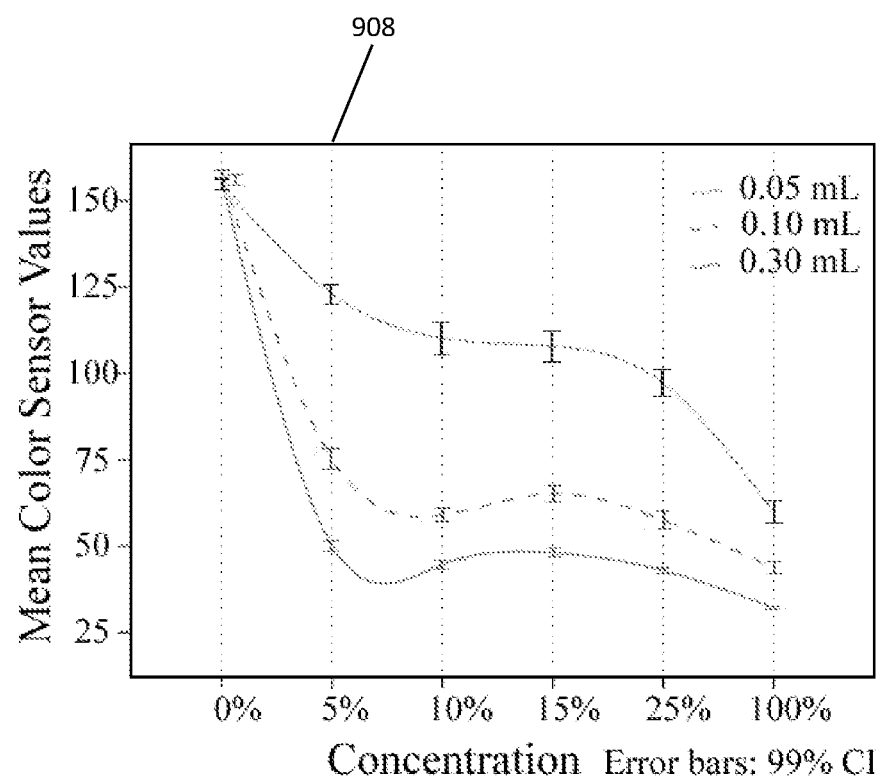
FIG. 9C is a graph showing the effectiveness of a first optical detector assembly in an exemplary embodiment in detecting different concentrations and volumes of carminic acid.

FIG. 9C is a graph showing the effectiveness of a first optical detector assembly in an exemplary embodiment in detecting different concentrations and volumes of carminic acid.

Carminic acid is a chemical solution which possesses light absorption characteristics which are similar to those of haemoglobin and may be used in place of haemoglobin to evaluate the performance of the optical detection assembly. As shown in FIG. 9B, in the optical window between 480 nm to 640 nm, carminic acid exhibits similar levels of light absorption as compared to haemoglobin and significantly higher levels of light absorption as compared to urine and water. Therefore, carminic acid may be suitable as a substitute for blood to evaluate the effectiveness of the optical detector assembly in the exemplary embodiment as shown in FIG. 9C.

In the exemplary embodiment, the optical detector assembly is configured to emit and detect electromagnetic waves at a wavelength of about 528 nm. The mean colour sensor values at a wavelength of 528 nm depend on the volume and concentration of carminic acid. FIG. 9C demonstrates that the colour sensor of the optical detector assembly is sensitive to both the volume and concentration levels. It is observed that in cases where the concentration of carminic acid is low e.g. 5%, the optical detector assembly is still capable of triggering a response given the presence of a substantial volume of carminic acid or artificial blood e.g. 0.10 ml to 0.30 mi. Compare the 5% line at numeral 908.

Figure 10A:
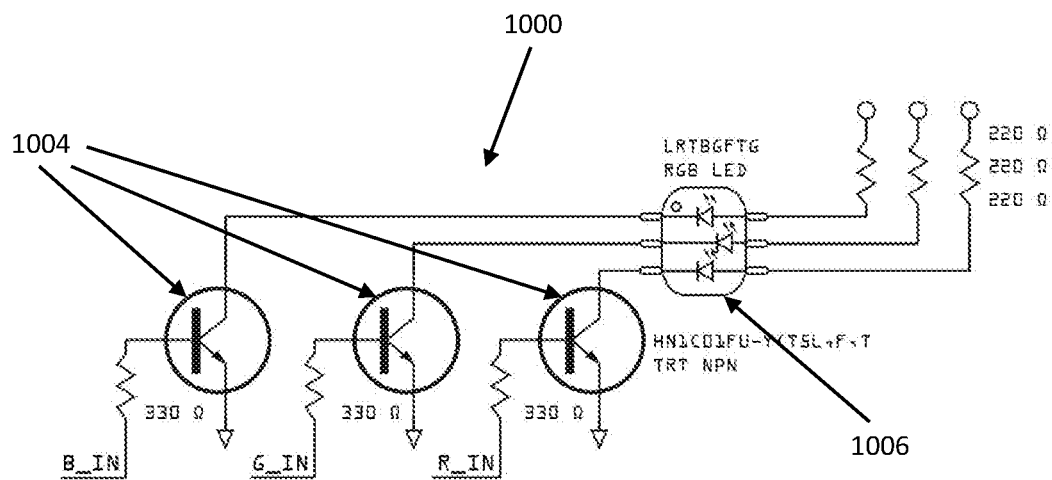
FIG. 10A is a schematic circuit diagram of a RGB LED in an exemplary embodiment.

FIG. 10A is a schematic circuit diagram of a RGB LED 1000 in an exemplary embodiment. The RGB LED 1000 can function as an EM wave emitter (e.g. model no. LRTBGFTG T7AW) of a first optical detector assembly that functions substantially similarly to the first optical detector assembly 104 of FIG. 1 and the first optical detector assembly 206 of FIG. 2B.

Figure 10B:
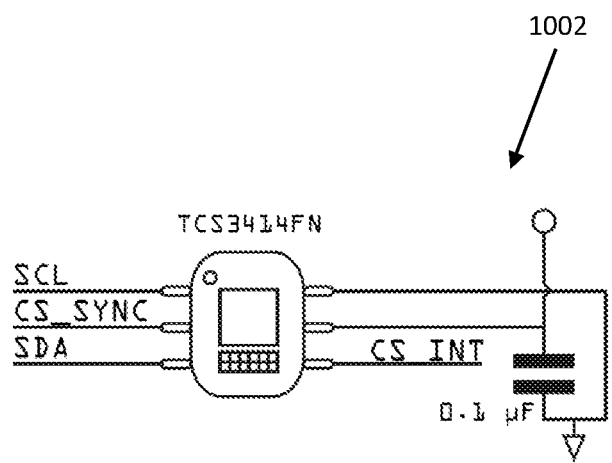
FIG. 10B is a schematic circuit diagram of a colour sensor in an exemplary embodiment.

FIG. 10B is a schematic circuit diagram of a colour sensor 1002 in an exemplary embodiment. The colour sensor 1002 can function as an EM wave detector (e.g. model no. TCS3414FN) of a first optical detector assembly that functions substantially similarly to the first optical detector assembly 104 of FIG. 1 and the first optical detector assembly 206 of FIG. 2B.

The RGB LED emitter 1000 comprises transistors e.g. 1004 each connected to a red, blue and green colour input channel respectively. The RGB LED emitter 1000 is configured to emit EM waves at about 470 nm, about 528 nm and about 625 nm. In the exemplary embodiment, the relative intensities of the three colour input channels can be independently controlled such that the RGB LED emitter 1000 emits substantially at a wavelength of about 528 nm. The transistors 1004 are connected to provide RGB LEDs 1006 with a suitable amount of current. The transistors 1004 are configured to drive each LED of the RGB LED 1006 directly from an energy supply source (not shown). The values for the resistors in the RGB LED emitter 1000 are selected in order not to saturate the colour sensor 1002 with electromagnetic waves.

The intensity of the RGB LED emitter 1000 is determined based on the following equations:

$$\text{Intensity In} = \frac{3.3\,\text{V}}{330\,\Omega} = 10\ \text{mA}$$

$$\text{Intensity Out} = \frac{3.3\,\text{V} - VCE(Sat) - VLED}{220\,\Omega}$$

$$\text{Intensity Out} = \frac{3.3\,\text{V} - 0.1\,\text{V} - 1.8\,\text{V}}{220\,\Omega} = 6\ \text{mA}$$

The colour sensor 1002 is configured to detect at three wavelengths of about 640 nm (red), about 524 nm (green) and about 410 nm (blue). A signal which is detected by the colour sensor 1002 is decomposed into measured intensities corresponding to red, green and blue wavelengths of light. Thus, the colour sensor 1002 is capable of detecting light of wavelength of about 528 nm emitted by the RGB LED 1000.

In the following figures (FIG. 11A to FIG. 12), exemplary embodiments of a second optical detector assembly for detecting presence of a liquid based on one or more optical characteristics of the liquid are described. The second optical detector assemblies in the following exemplary embodiments function substantially similarly to the second optical detector assembly 216 of FIG. 2B. The second optical detector assembly may comprise a second EM wave emitter and a second EM wave detector. The second EM wave emitter may be an IR (infrared) emitter (e.g. model no. TSML1020) with a 30° beam angle centred at a wavelength of about 950 nm and the second EM wave detector may be a photodiode (e.g. model no. VBP104FAS) with a 130° viewing angle and configured to produce a maximum spectral response at about 950 nm.

Figure 11A:
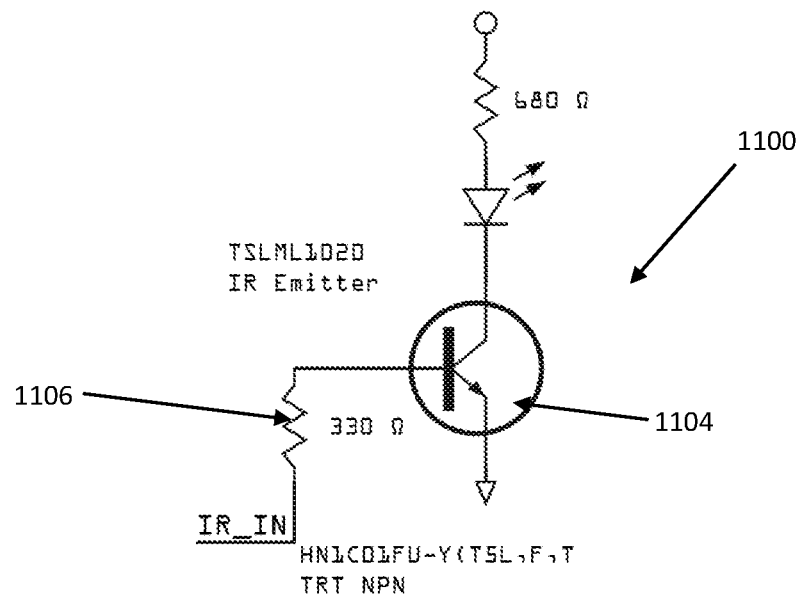
FIG. 11A is a schematic circuit diagram of an infrared (IR) LED emitter in an exemplary embodiment.

FIG. 11A is a schematic circuit diagram of an infrared (IR) LED emitter 1100 in an exemplary embodiment. The IR LED emitter 1100 can function as an EM wave emitter for a second optical detector assembly that functions substantially similarly to the second EM wave emitter 218 of the second optical detector assembly 216 of FIG. 2B.

Figure 11B:
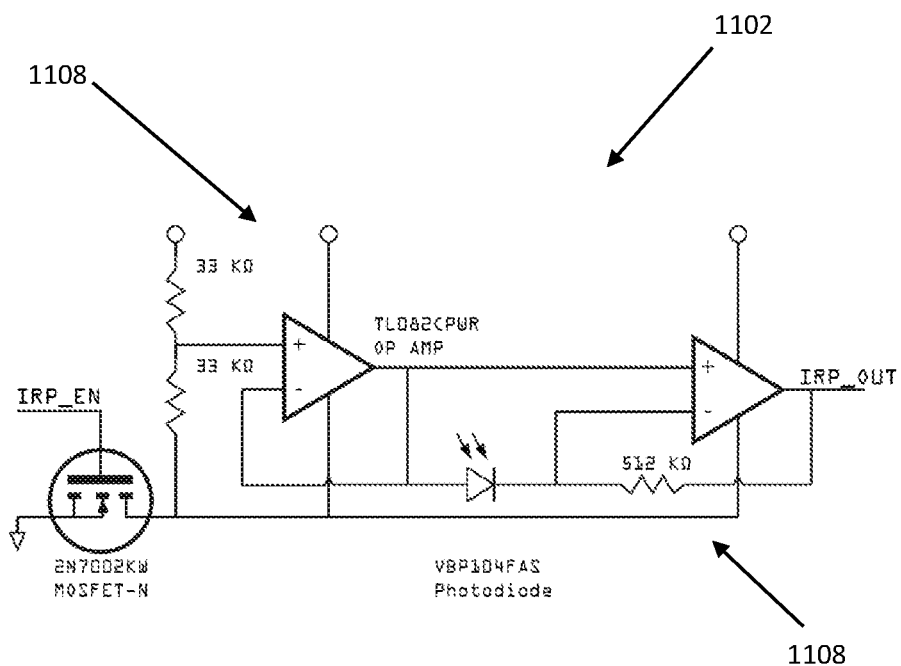
FIG. 11B is a schematic circuit diagram of a photodiode in an exemplary embodiment.

FIG. 11B is a schematic circuit diagram of a photodiode 1102 in an exemplary embodiment. The photodiode 1102 can function as an EM wave detector for a second optical detector assembly that functions substantially similarly to the second EM wave detector 220 of the second optical detector assembly 216 of FIG. 2B.

The IR LED emitter 1100 comprises a transistor 1104 for providing the IR LED 1100 with a suitable amount of current, and a resistor 1106 having a resistance such that the photodiode 1102 is not saturated by the infrared waves emitted by the IR LED 1100. The intensity of IR waves emitted by the IR LED emitter 1100 is determined based on the following equations:

$$\text{Intensity In} = \frac{3.3\,\text{V}}{330\,\Omega} = 10\ \text{mA}$$

$$\text{Intensity Out} = \frac{3.3\,\text{V} - VCE(Sat) - VLED}{680\,\Omega}$$

$$\text{Intensity Out} = \frac{3.3\,\text{V} - 0.1\,\text{V} - 1.2\,\text{V}}{680\,\Omega} = 3\ \text{mA}$$

The photodiode 1102 comprises a current-to-voltage single supply converter 1108 for transforming the current generated by the photodiode 1102 into a voltage which is fed to an analogue to digital (ADC) converter of a microcontroller (e.g. model no. NRF51822). The photodiode 1102 input is driven into a current-to-voltage converting amplifier (e.g. model no. TL082).

The relationship is as follows:

$V\text{out} = \text{Intensity Photodiode} \times R\text{Feedback}$ $R\text{Feedback} = 512\ \text{K}\Omega$ The photodiode 1102 further comprises a JFET OP Amp 1110 with low input current to obtain an improved gain with reduced noise. The area of the photodiode is about 4.4 mm$^2$.

The drawings of FIG. 11A and FIG. 11B show power supplied to power both the IR LED emitter 1100 and photodiode 1102. The components also function to provide an interface to a micro-controller (not shown).

Figure 12:
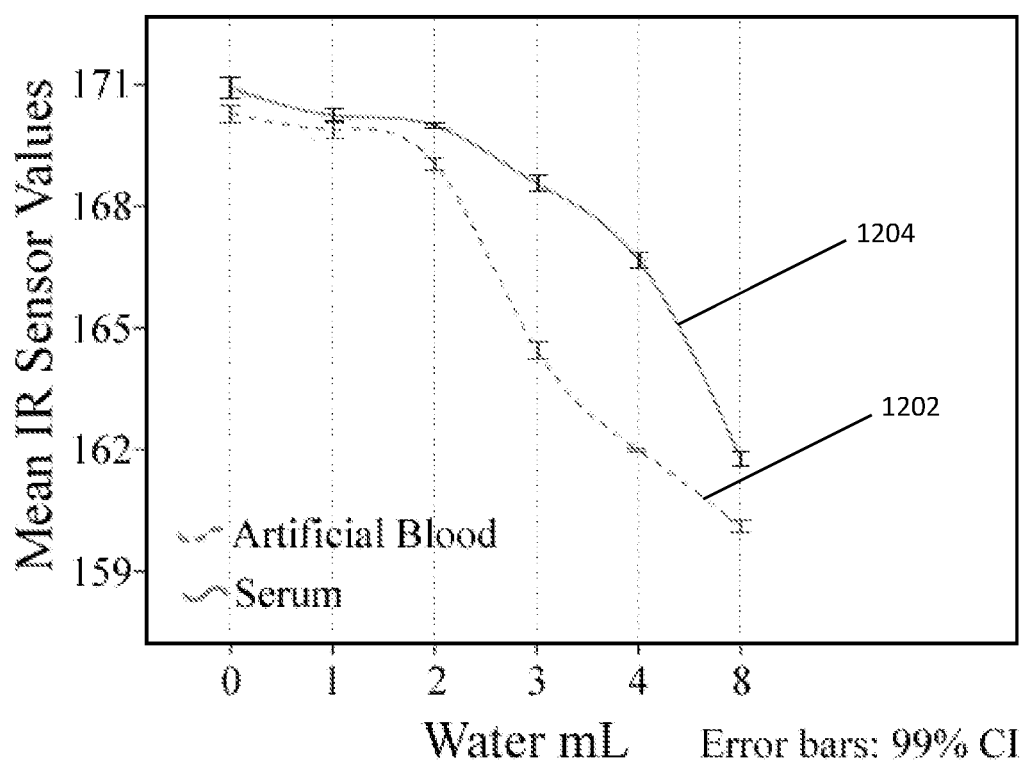
FIG. 12 is a graph showing the effectiveness of a second optical detector assembly in an exemplary embodiment in detecting presence of a liquid at different volumes.

FIG. 12 is a graph showing the effectiveness of a second optical detector assembly in an exemplary embodiment in detecting presence of a liquid at different volumes. As shown in FIG. 12, the second optical detector assembly is used to detect presence of artificial blood (e.g. carminic acid) and serum. The artificial blood used is carminic acid, which exhibits similar absorption characteristics with haemoglobin.

Between 0 mL and 2 mL, the mean IR sensor values determined at the second optical detector assembly do not change significantly. From 3 ml to 8 ml, the mean IR sensor values are significantly lower as compared to values at 0 ml, thus indicating the presence of liquid i.e. serum and artificial blood. Therefore, the second optical detector assembly in the exemplary embodiment is suitable for detecting presence of liquid when the quantity of liquid present is at least 3 ml. The inventors have recognised that, in practice, the second optical detector assembly may be useful in detecting presence of liquid in a bandage dressing when the bandage dressing is substantially soaked with liquid. It is observed that the results show that for the same volume of liquid, the mean IR sensor values decrease to a greater extent in the presence of absorbent substances such as carminic acid (see 1202) than as compared to serum (see 1204). This demonstrates that the second optical detector assembly may be triggered at relatively lower volumes and with improved contrast for liquids that are different from water ($H_2O$) since serum comprises $H_2O$ as a major component.

Therefore, the second optical detector assembly may be useful for detection of diluted blood and other fluids. For example, the second optical detector assembly may be useful when a change of dressing is required. In order to effectively detect the presence of a liquid based on its optical characteristics, an optimal working wavelength that allows detection of aqueous solutions is desired. Based on FIG. 9A, it is observed that $H_2O$ or water exhibits a peak in EM wave absorption in the infrared region. Therefore, a wavelength of from about 900 nm to about 1000 nm, or preferably about 950 nm, is chosen to be used in the second optical detector assembly for detecting presence of liquid based on its absorption characteristics at 950 nm.

In the following figures (FIG. 13 to FIG. 14), different exemplary embodiments of power sources for an on-site device for detecting presence of liquid from a site are described. The on-site device may operate as a stand-alone device capable of efficient energy consumption. A 110 mAh battery may be used to power the on-site device. The average power consumption of the on-site device is approximately 60 mAh. The rate of power consumption depends on the power usage of individual components such as the moisture detector, the first optical detector assembly, the second optical detector assembly and the alarm circuit.

The battery of the on-site device may be configured to last up to 8 hours if the moisture detector and the second optical detector assembly are active, and the first optical detector assembly is not activated. In their active states, the moisture detector and the second optical detector assembly are turned on to detect presence of a liquid. For example, the second EM wave emitter of the second detector assembly may transmit pulses of EM waves every 50 milliseconds or every 100 milliseconds, each time consuming up to about 60 mA. For example, the moisture detector may consume about 10 mA.

Similarly, upon activation of the first optical detector assembly, the first EM wave emitter of the first optical detector assembly may transmit pulses of EM waves every 50 milliseconds or every 100 milliseconds, each time consuming up to about 60 mA. In this activated state of the first optical detector assembly, the battery of the on-site device decreases significantly but is still capable of lasting at least 1 hour. To conserve power, the first EM wave emitter and first EM wave detector of the first optical detector assembly is activated after presence of moisture/liquid is detected.

The on-site device may be charged in different ways. In one exemplary embodiment of the on-site device, non-inductive charging may be implemented to charge the on-site device.

Figure 13:
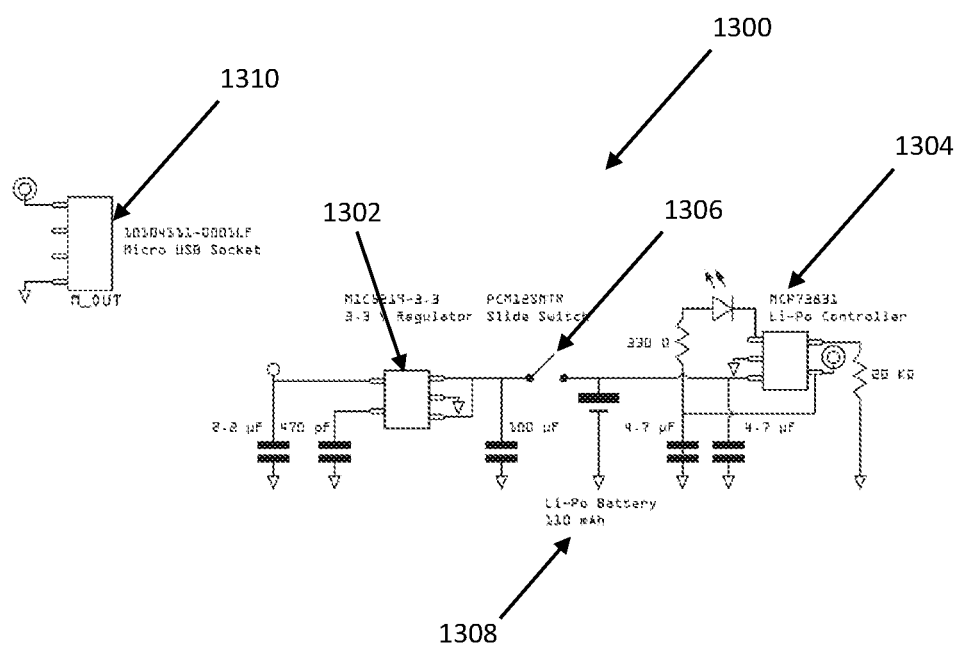
FIG. 13 is a schematic circuit diagram of a non-inductive charging power source in an exemplary embodiment.

FIG. 13 is a schematic circuit diagram of a non-inductive charging power source 1300 in an exemplary embodiment. The non-inductive charging power source 1300 comprises a regulator 1302, a battery manager 1304, a slide switch 1306 (e.g. model no. PCM12SMTR slide switch) and a lithium ion polymer (Li-Po) battery 1308. The regulator 1302 is a 3.3 V regulator configured to maintain a constant power supply by the Li-Po battery 1308 (typically 3.7V). The battery manager 1304 is a MCP73831 linear charge management controller for re-charging the Li-Po battery at 50 mAh. The non-inductive charging power source 1300 further comprises a 10104111-10001LF micro USB socket for connecting to a microcontroller (not shown). In the exemplary embodiment, a mechanism is provided for power from an electric power source e.g. wall outlet to be supplied through a micro Universal Serial Bus (USB) port 1310 (5V) and managed by the battery manager 1304 to charge an on-board Li-Po battery 1308.

In another exemplary embodiment, inductive charging may be implemented to charge the on-site device.

Figure 14:
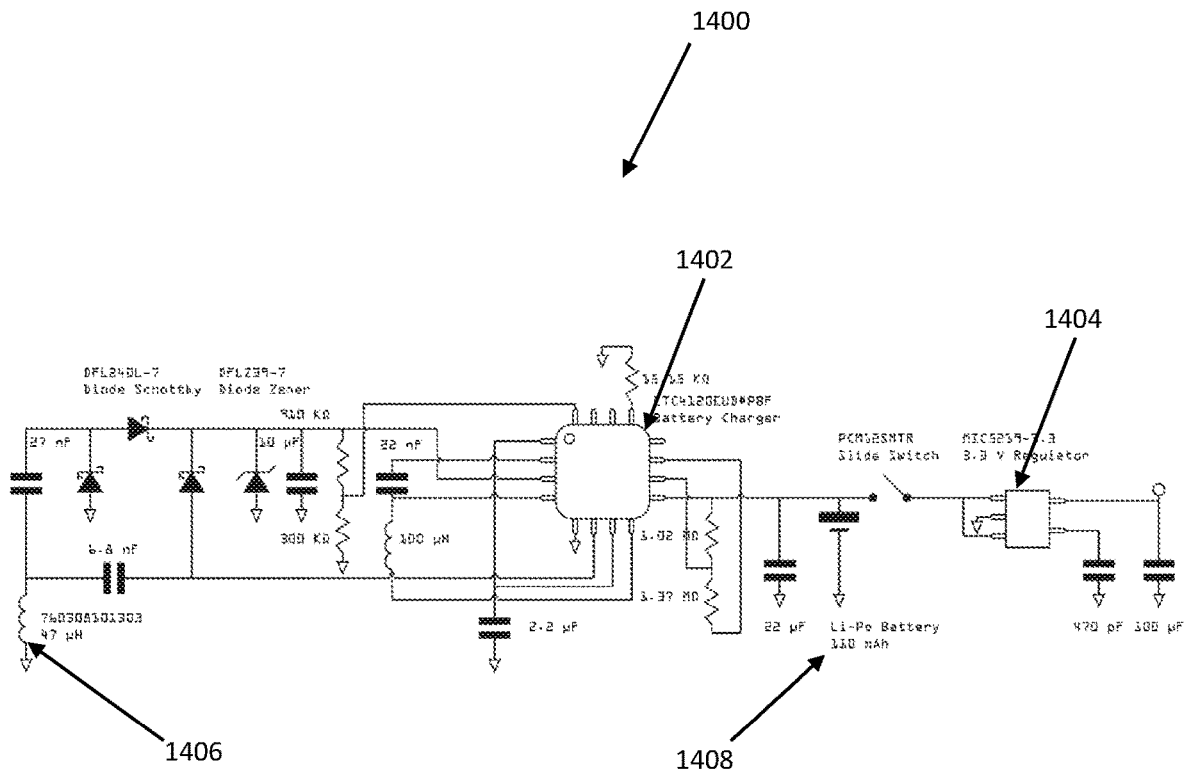
FIG. 14 is a schematic circuit diagram of an inductive charging power source in an exemplary embodiment.

FIG. 14 is a schematic circuit diagram of an inductive charging power source 1400 in an exemplary embodiment. The inductive charging power source 1400 comprises a battery manager 1402, a regulator 1404, a receiver coil 1406 and a Li-Po battery 1408. In the exemplary embodiment, wireless charging of the Li-Po battery 1408 at 82 mAh is achieved by using the battery manager 1402 (e.g. model no. LTC4120EUD#PBF) and a wireless charging optimizer in conjunction with a resonant circuit. The receiver coil 1406 has an inductance of 47 µH and is capable of tolerating currents up to 1.5 A. The resonant frequency is chosen to be 127 KHz, such that the resonant circuit is compatible with existing components that are available commercially. The capacitors in the resonant circuit are chosen to have matching values with less than 1% tolerances. The regulator 1404 is a MIC5219-3.3 3.3 V regulator and functions to maintain a constant power supply by the Li-Po battery (typically 3.7V).

In the on-site device of described exemplary embodiments, a microcontroller may be used to control the functions of various components of the on-site device. For example, a NRF51822 system on chip (SoC) may be used. In the described exemplary embodiments, a microcontroller may be coupled to the moisture detector, the first optical detector assembly, the second optical detector assembly, the power source and the alarm circuit. The microcontroller may be configured to control e.g. the EM waves emissions, the EM waves detections, activation of the first optical detector assembly, generating/triggering of alert signals etc. In the exemplary embodiments, the microcontroller may function as a processor or processing module of the on-site device.

Figure 15A:
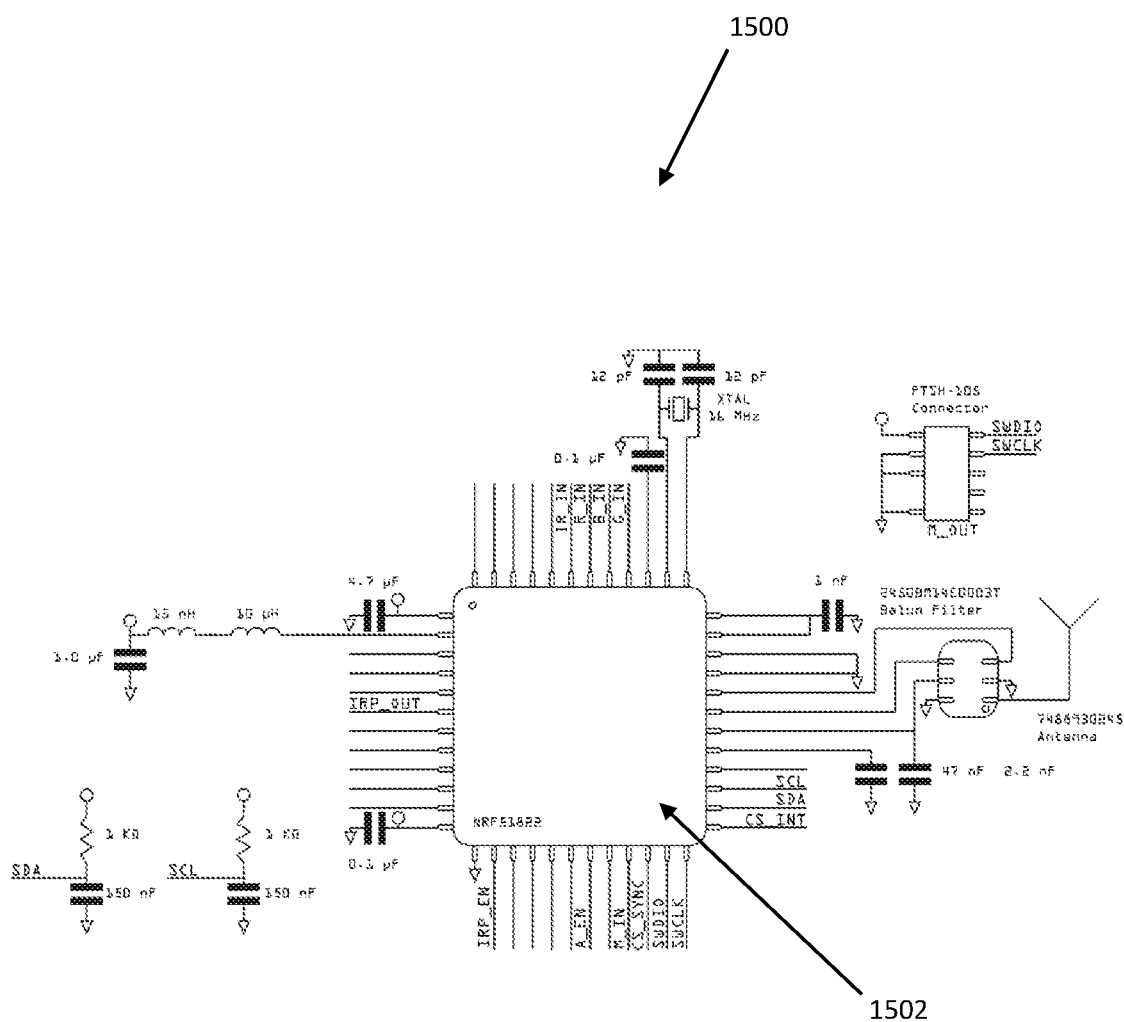
FIG. 15A is a schematic circuit diagram of a microcontroller for an on-site device in an exemplary embodiment.

FIG. 15A is a schematic circuit diagram of a microcontroller 1500 for an on-site device in an exemplary embodiment. The microcontroller 1500 is configured for an on-site device which uses a moisture detector based on a resistive sensing approach. The microcontroller 1500 comprises a NRF51822 system on chip (SoC) 1502 configured to have a low energy consumption ARM MO-Cortex processor incorporating Bluetooth Low Energy (LE) for communication. The NRF51822 system on chip (SoC) 1502 has an operating frequency of 16 MHz, a 32-bits architecture, 31 GPIO (general purpose input/output) and 8 ADC (analogue to digital converter) with up to 10 bits of resolution.

Figure 15B:
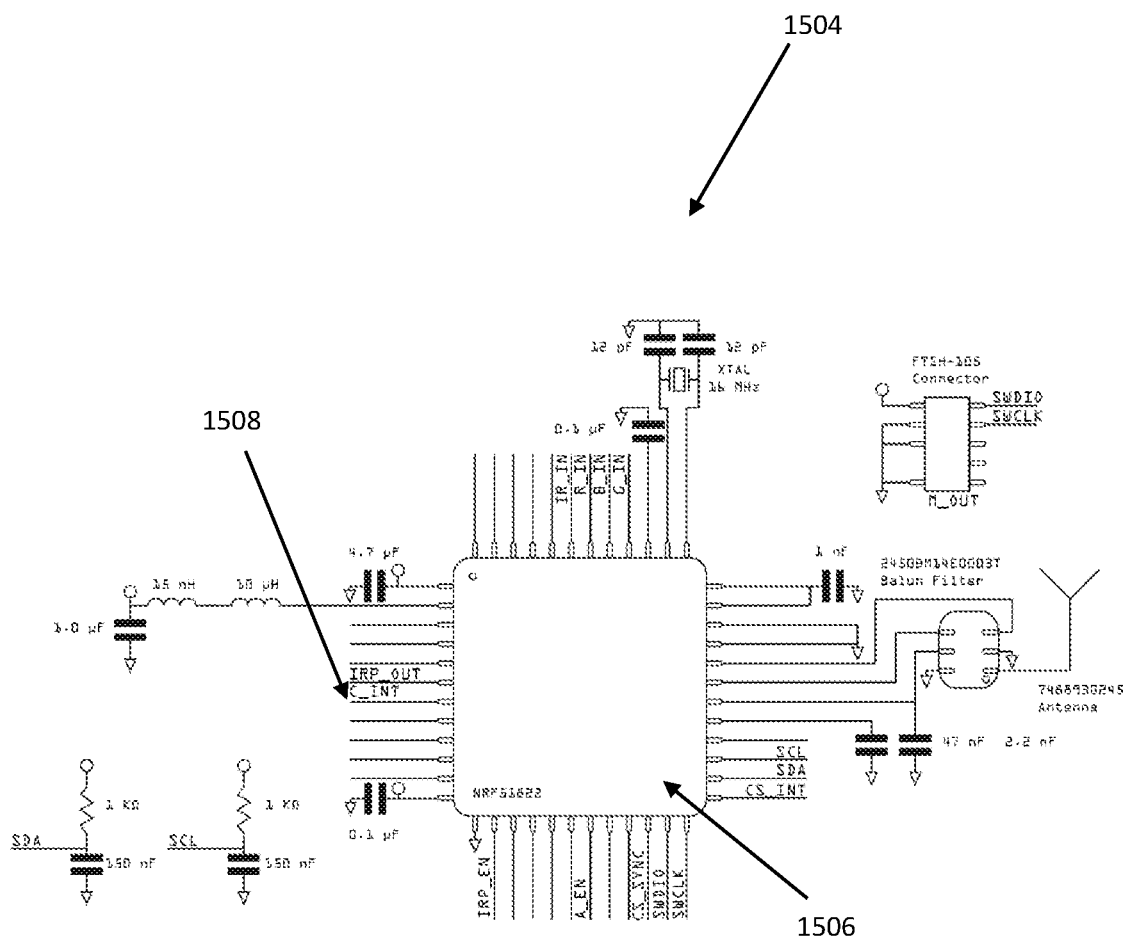
FIG. 15B is a schematic circuit diagram of a microcontroller for an on-site device in an exemplary embodiment.

FIG. 15B is a schematic circuit diagram of a microcontroller 1504 for an on-site device in an exemplary embodiment. The microcontroller 1504 is configured for an on-site device which uses a moisture detector based on a capacitive sensing approach. The microcontroller 1504 comprises a NRF51822 system on chip (SoC) 1506 which is substantially similar to the NRF51822 system on chip (SoC) 1502 of FIG. 15A, except for a C_INT terminal 1508 which enables the on-site device to detect presence of a liquid using a capacitive sensing approach.

In the exemplary embodiments, upon detection of haemoglobin by the first optical detector assembly and/or upon detection of the presence of liquid by the second optical assembly, an alert or alarm signal may be generated.

Figure 16:
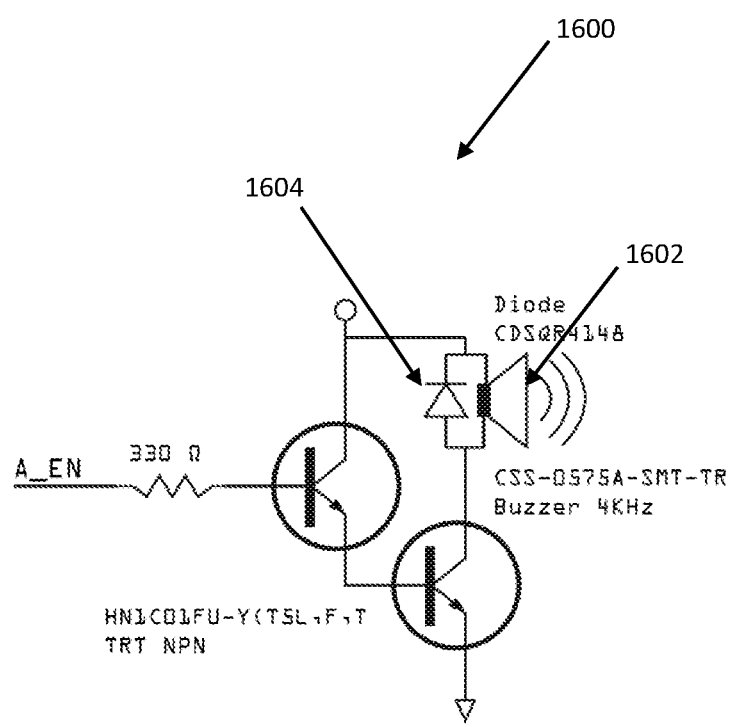
FIG. 16 is a schematic circuit diagram of an alarm circuit for an on-site device in an exemplary embodiment.

FIG. 16 is a schematic circuit diagram of an alarm module/circuit 1600 for an on-site device in an exemplary embodiment. The alarm module/circuit 1600 comprises a Darlington configuration having an alarm or a buzzer 1602 which is configured to allow a suitable amount of current to pass through. The buzzer 1602 is a 75 dB magnetic buzzer transducer (CSS 0575A) configured to resonate at 4.000 Hz. In the exemplary embodiment, the alarm circuit 1600 further comprises a protection diode 1604. The protection diode 1604 functions to protect the alarm circuit 1600. When the buzzer 1602 is activated, an inductive load is generated across the alarm circuit 1600. This may create relatively large voltages which may in turn damage the alarm 1600 circuit. To avoid damaging the alarm circuit 1600, the protection diode 1604 is added to dissipate the relatively large voltages. The alert signal may be output by a microcontroller at A_EN.

In the exemplary embodiment, the current flowing through the alarm circuit 1600 is 10 mA as shown in the calculation below.

$$\text{Intensity In} = \frac{3.3 \text{ V}}{330 \Omega} = 10 \text{ mA}$$
$$\text{Intensity Out} = \beta_1 \cdot \beta_2 \cdot \text{Intensity In}$$

In the exemplary embodiment, the alarm module 1600 is coupled to the first optical detector assembly. The alarm module 1600 is configured to trigger an alarm signal upon detection of the presence of the substance in the liquid by the first optical detector assembly via A_EN. The alarm signal can activate the alarm or the buzzer 1602.

Figure 17:
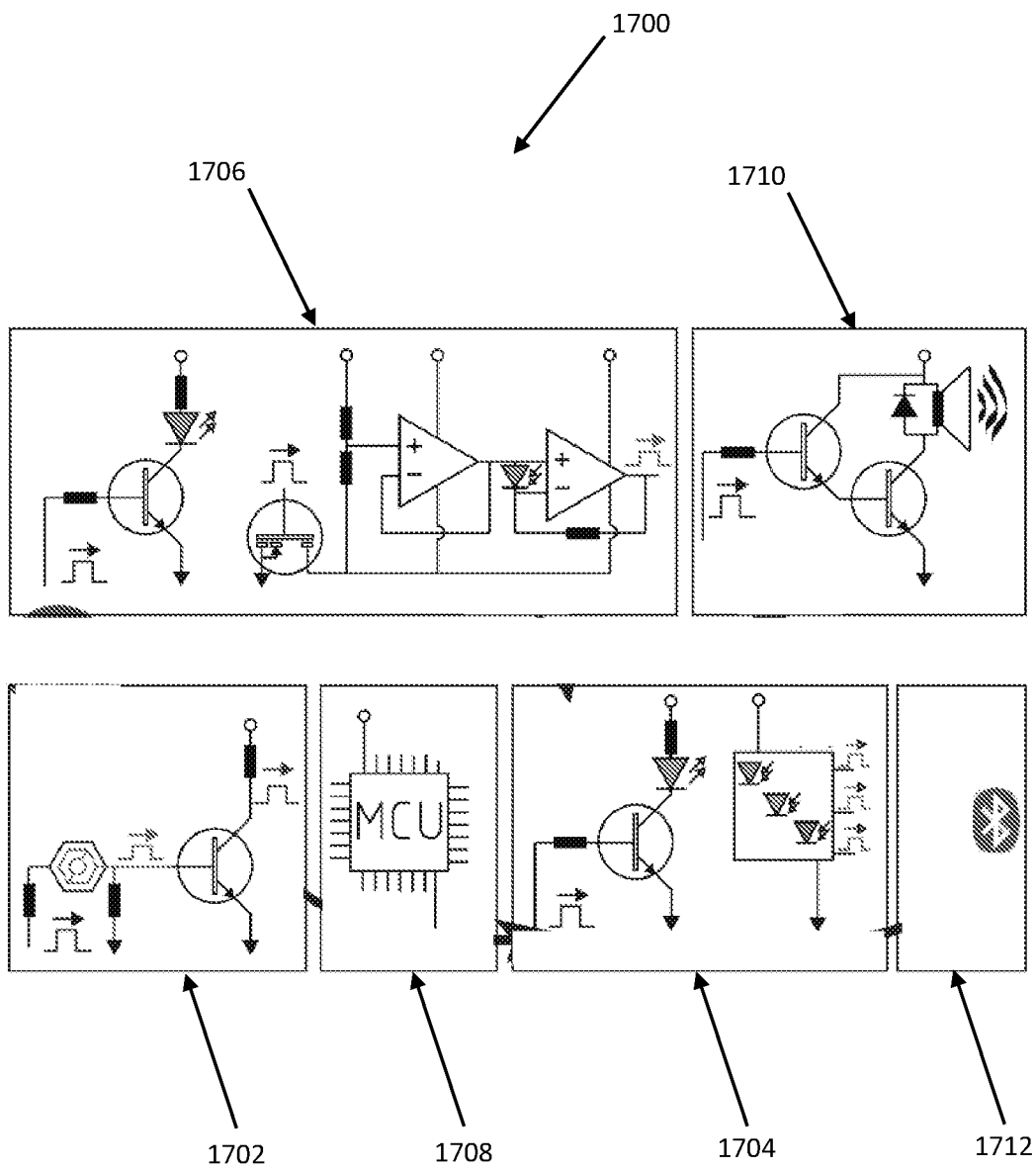
FIG. 17 is a schematic diagram for illustrating an operation of an on-site device for detecting presence of a liquid from a site in an exemplary embodiment.

FIG. 17 is a schematic diagram for illustrating an operation of an on-site device 1700 for detecting presence of a liquid from a site in an exemplary embodiment. The on-site device 1700 comprises a moisture detector 1702, a first optical detector assembly 1704, a second optical detector assembly 1706, a microcontroller unit 1708, an alarm module/circuit 1710 and a BLE (Bluetooth Low Energy) module 1712.

The moisture detector 1702 functions substantially similarly to the moisture detector 306 of FIG. 3B and is configured to detect presence of liquid using a resistive sensing technique.

The first optical detector assembly 1704 functions substantially similarly to the first optical detector assembly 800 of FIG. 8A and is configured to detect presence of haemoglobin based on the light absorption characteristic of haemoglobin.

The second optical detector assembly 1706 functions substantially similarly to the second optical assembly 216 of FIG. 2B and is configured to detect presence of a liquid based on one or more optical characteristics of the liquid.

The microcontroller unit 1708 functions substantially similarly to the microcontroller 1500 of FIG. 15A The alarm module/circuit 1710 functions substantially similarly to the alarm circuit 1600 of FIG. 16 and is configured to set off an alarm of the on-site device 1700.

The BLE module 1712 is configured to receive an alarm signal from the alarm module/circuit 1710 and to trigger an alert signal to be transmitted to an alarm monitoring remote system via wireless transmission such as via low energy Bluetooth. The alarm signal is trigger upon detection of the presence of haemoglobin at a site e.g. on a surface of a bandage dressing.

The on-site device 1700 is applied onto a surface of a bandage dressing covering a site where there may be occurrence of bleeding, e.g. a catheter insertion/in-dwell/removal site. The on-site device 1700 is positioned in close proximity to the site, preferably on the surface of the bandage dressing directly above the site so that any bleeding can be detected in a relatively shorter time as compared to a position which is further from the site. A secondary dressing may be applied to immobilize the on-site device 1700 at its position.

In use, the moisture detector 1702 periodically detects for presence of liquid by sending electric pulses at a frequency of 10 Hz. Concurrently, the second optical detector assembly 1706 periodically detects for presence of a liquid by transmitting pulses of electromagnetic waves having a wavelength centred at about 950 nm towards the surface of the bandage dressing.

In the event of bleeding, the bandage dressing covering the site contains blood and blood may reach the surface of the bandage dressing where the on-site device 1700 is positioned. The presence of the liquid or blood is detected by the moisture detector 1702 and/or the second optical detector assembly 1706, which then transmits a signal to the microcontroller 1708 indicating the presence of a liquid.

Upon detecting the presence of a liquid (e.g. blood), the microcontroller 1708 sends a signal to activate the first optical detector assembly 1704 to detect for the presence of haemoglobin in the liquid.

Upon activation, an EM wave emitter of the first optical detector assembly 1704 begins to transmit pulses of light having wavelengths centred at about 470 nm, about 528 nm and about 625 nm towards the surface of the bandage dressing. An EM wave detector of the first optical detector assembly 1704 begins to detect for light with wavelengths centred at about 470 nm, about 524 nm and about 640 nm, in particular, light reflected from the surface of the bandage dressing.

If haemoglobin is present in the liquid, the amount of light at the above wavelengths being reflected from the surface of the bandage dressing and subsequently detected by the EM wave detector decreases due to absorption by the haemoglobin in the liquid. If the amount of light detected by the EM wave detector of the first optical detector assembly 1704 falls below a predetermined threshold level, a signal is triggered and sent to the microcontroller 1708 to indicate the presence of haemoglobin, and indicating that the detected liquid is blood.

Upon detecting the presence of haemoglobin, a signal is triggered by the microcontroller 1708 to activate the alarm module/circuit 1710. The alarm module/circuit 1710 triggers an alarm signal to activate an alarm or buzzer of the on-site device 1700. The alarm signal also triggers an alert signal to be sent by the microcontroller 1708 to a remote system via the BLE module 1712, i.e. via wireless transmission.

Figure 18:
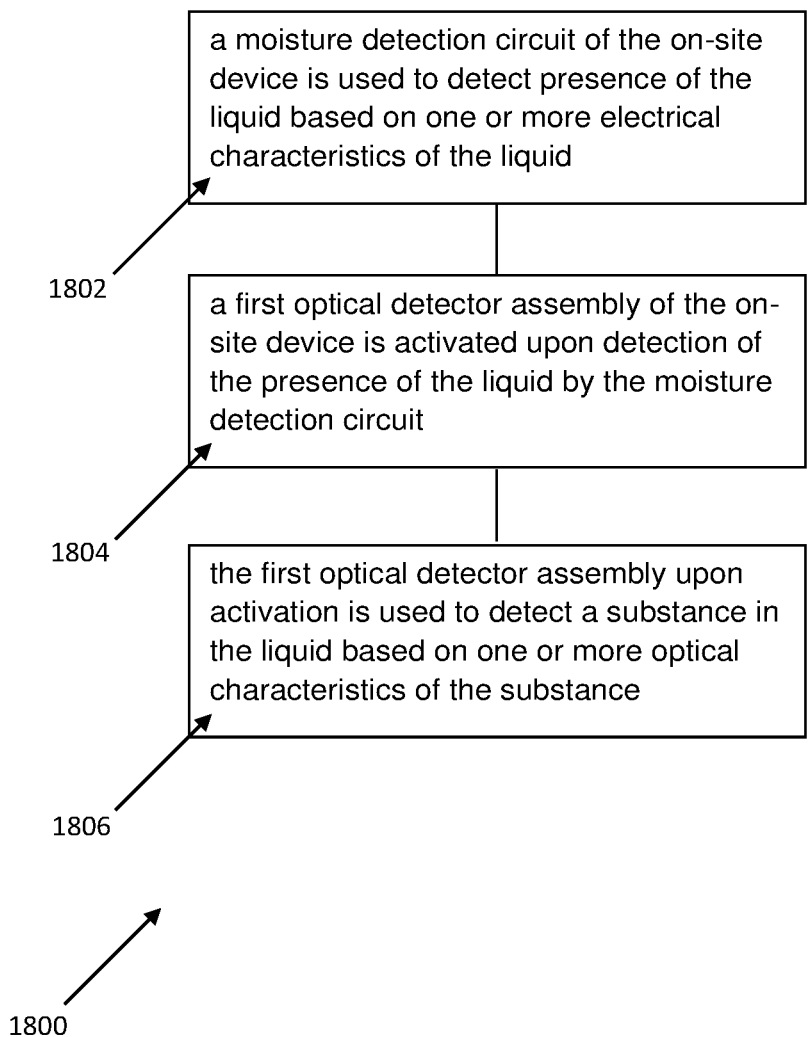
FIG. 18 is a schematic flowchart for illustrating a method for detecting presence of a liquid from a site using an on-site device in an exemplary embodiment.

FIG. 18 is a schematic flowchart 1800 for illustrating a method for detecting presence of a liquid from a site using an on-site device in an exemplary embodiment. At step 1802, a moisture detector of the on-site device is used to detect presence of the liquid based on one or more electrical characteristics of the liquid. At step 1804, a first optical detector assembly of the on-site device is activated upon detection of the presence of the liquid by the moisture detector. At step 1806, the first optical detector assembly upon activation is used to detect a substance in the liquid based on one or more optical characteristics of the substance.

Figure 19:
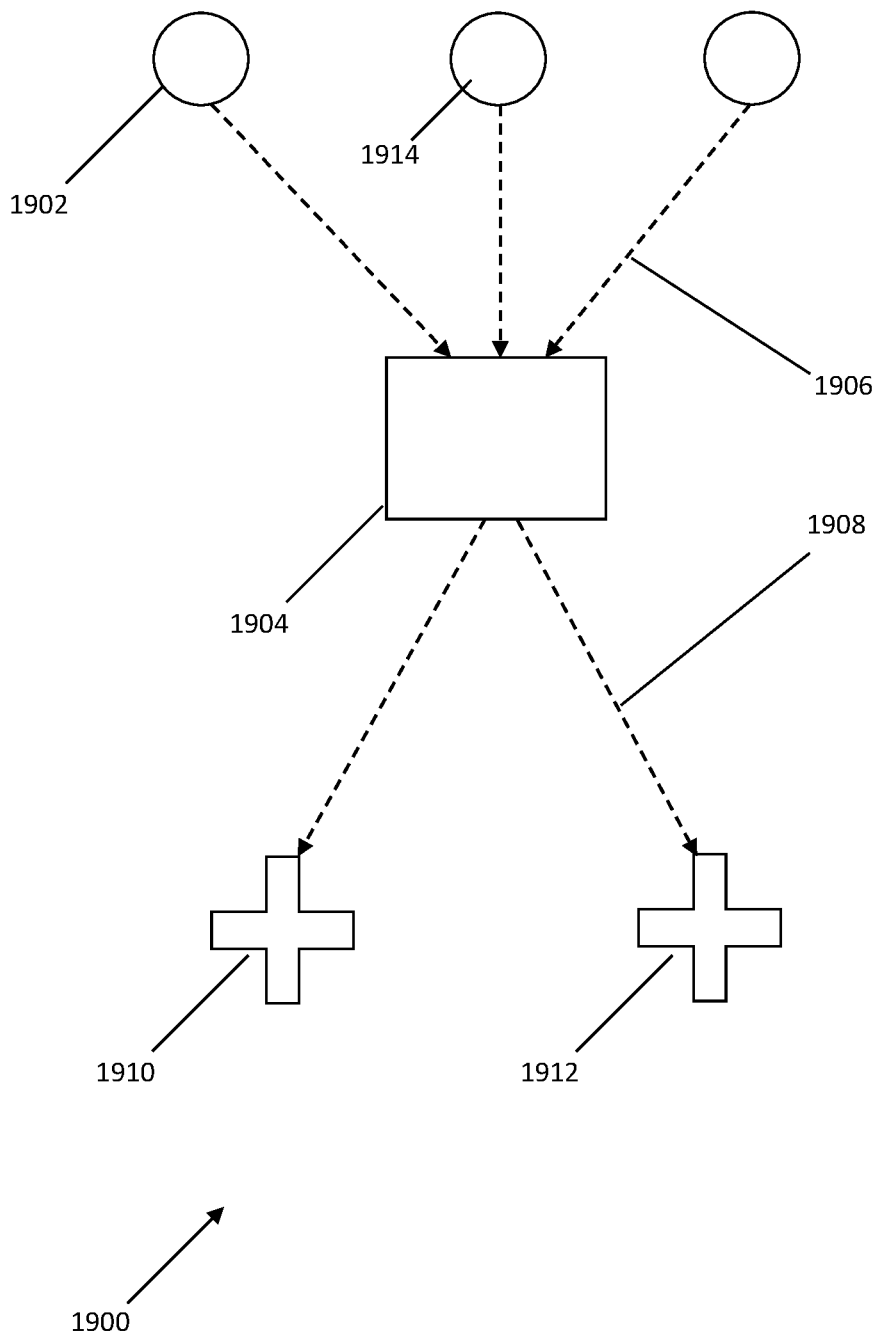
FIG. 19 is a schematic diagram of a warning system for detecting presence of a liquid from one or more sites in an exemplary embodiment.

FIG. 19 is a schematic diagram of a warning system 1900 for detecting presence of a liquid from one or more sites in an exemplary embodiment. The warning system 1900 comprises one or more on-site devices 1902, 1914 for detecting presence of a liquid from one or more sites and an alarm monitoring remote system 1904 configured to receive one or more alert signals 1906 from the one or more on-site devices 1902, 1914. Upon receipt of the one or more alert signals 1906, the alarm monitoring remote system 1904 is arranged to trigger an alarm to indicate the presence of liquid from the one or more sites 1902, 1914.

In the exemplary embodiment, the alarm triggered at the alarm monitoring remote system 1904 is configured to trigger one or more alarms 1908 at one or more personnel stations 1910 or one or more alerting devices 1912 carried by medical personnel, or even both, to indicate the presence of liquid at the one or more sites.

The one or more alert signals 1906 may be arranged to be transmitted by wireless technology such as Bluetooth BLE to the alarm monitoring remote system 1904.

In addition, repeaters (not shown) may be provided between the one or more on-site devices 1902, 1914 and the alarm monitoring system 1904 to improve the transmission of signals. The one or more alarms 1908 may be arranged to be transmitted by wireless technology such as Bluetooth LE, Wi-Fi, or telecommunication technology such as short messaging system.

Exemplary embodiments of the disclosure will be better understood with the following examples, which describe experiments to assess the effectiveness of an on-site device for detecting presence of liquid from a site.

Four experiments were conducted. A first experiment tested the effectiveness of a moisture detector which is based on resistive sensing. A second experiment evaluated the performance of the optical detector assembly emitting light at about 528 nm in its ability to differentiate between different kinds of fluids. A third experiment analysed the capabilities of the optical detector assembly emitting light at about 950 nm as a liquid detector. A fourth experiment studied the performance of the on-site device in the presence of blood collected from a human body.

For the first three experiments, gauzes of 7×7 cm were organized in columns of six rows. Depending on the number of dimensions of the experiment, more columns were added (e.g. rows represent the volume of a certain fluid while each column represents a different fluid). A total of 300 samples were taken per column (i.e. fifty sets, each consisting of six readings, one for each row).

In the first experiment, the purpose is to demonstrate the ability of a moisture detector (resistive electric circuit e.g. compare moisture detector 400 of FIG. 4) to activate upon detecting the presence of fluid. A presumption behind the first experiment is that if the moisture detector is sensitive enough to detect water, it is reasonable to infer that the presence of the other body fluids with a relatively higher conductivity can effectively trigger the moisture detector to produce a response.

To evaluate the humidity sensitivity, dressing soaked with different volumes of water or $H_2O$ were tested. Six gauzes of 7×7 cm, each having a different liquid volume, were placed over a non-absorbent acrylic surface for the bandage to absorb the fluid. After 1 minute, a total of three hundred samples were collected. Fifty sample sets consisting of six readings each were taken, one for each volume. Before each reading, excess humidity on the moisture detector was removed before being randomly positioned over the next dressing.

A one way ANOVA with a Bonferroni correction and a confidence level of 99% was used to analyse the statistical significance of each interaction. The findings were plotted on a bar chart as shown in FIG. 7 and show a mean effect for water volumes. Post-hoc analysis shows that the moisture detector or sensor can be triggered by any of the liquid volumes under test with a minimum mean difference of 28.56 (SE=2.794, p<0.01). Thus, the sensor can be configured to be triggered at different levels of humidity. The threshold level of the sensor was set to 200.

In the second experiment, the effectiveness of an optical detector assembly using 528 nm wavelength of light as a distinctive artificial blood-serum differentiator was investigated. The first validation factor for the optical detector assembly is to be sensitive enough to reveal significantly small amounts of blood (i.e. in the order of millilitres, ml). The second factor focuses on a common condition, i.e. when the blood is diluted and the haemoglobin and haematocrit levels are lower than normal levels.

Artificial blood comprising an aqueous solution of carminic acid was used to mimic blood. Although there is no haemoglobin present in the artificial blood used, carminic acid solution exhibits similar levels of absorbance at a wavelength of 528 nm.

Eighteen gauzes of 7×7 cm were positioned over a non-absorbent acrylic surface in a matrix of 6 rows by 3 columns. Under the acrylic, dry and sterile gauzes were placed to avoid undesired absorptions or reflections from the surface of the table. Each row represents a different concentration of artificial blood with 0.01 mL diluted according to the following ratios [artificial blood: serum]: [0:1] [1:20], [1:10], [1:7], [1:4] and [1:0]. Each column contains a different volume of the solution, 0.005 mL, 0.01 mL and 0.03 mL respectively. Next, a total of nine hundred samples was acquired. Fifty sample sets were collected for each column and only one column was tested at a time. Each one of the fifty sample sets consist of six readings, one for each concentration were taken.

A two way ANOVA with a Bonferroni correction and a confidence level set to 99% was used to analyse the statistical significance of each interaction. The results (as shown in FIG. 9C) are statistically significant across all conditions and reveal that even with the smallest tested amount of volume and blood concentration, the fluid differentiation is still substantial. For instance, at 0.05 mL volume, the minimum mean difference between 0% blood concentration and 5% is 31.820 (SE=1.358, p<0.01). Therefore, the optical detector assembly using 528 nm wavelength of light or sensor is sensitive both to the volume and concentration levels. Even in the case whereby the concentration of carminic acid is low at about 5%, the optical detection assembly is still able to trigger a response provided that a limited volume e.g. 0.3 ml of artificial blood is present.

In the third experiment, the effectiveness of the optical detector assembly using 950 nm wavelength to detect the presence of liquid on the dressing was analysed. Haemoglobin, urine and carminic acid (artificial blood) show significant light absorbance at this frequency. Assuming that these substances are always dissolved in aqueous solutions, the test was performed using serum, which is substantially the same as salt water.

Twelve gauzes of 7×7 cm were positioned over a non-absorbent transparent acrylic sheet in a matrix of 6 rows by 2 columns. Under the acrylic, dry and sterile gauzes were placed to avoid undesired absorptions or reflections from the surface of the table. Each row represents a different volume of liquid. Each column contains a different substance. One contains serum and the other contains non-diluted artificial blood. A total of six hundred samples were collected. Fifty sample sets were collected for each column and only one column was tested at a time. Each one of the fifty sample sets consist of six readings, one for each volume. Between readings, the on-site device was cleaned, removed and then randomly positioned over the next dressing.

A two way ANOVA with a Bonferroni correction and a confidence level of 99% was used to analyse the statistical significance of each interaction. The results (as shown in FIG. 12) are statistically significant and indicate that the optical detector assembly using 950 nm wavelength to detect moisture is reliable when the dressing is soaked with a volume of liquid, i.e. at least 3 ml of liquid. Hence, a confidence threshold could be set at 3 mL volume level at which the mean difference between the dry dressing is 4,090 (SE=0.07, p<0.01). The results also suggest that luminous intensity decreases more significantly in the presence of absorbent substances such as carminic acid as compared to water or serum. This demonstrates that for liquids apart from water, the infrared sensor may be triggered to detect presence of the liquid at lower volumes e.g. 3 ml, and allows for an improved contrast.

In the fourth experiment, the performance of the on-site device in detecting the presence of blood collected from a human body is tested. Compare on-site device 200 of FIG. 2B. A preliminary evaluation was conducted using three blood samples from different haemodialysis patients. Due to the short shelf-life of the samples, one set of readings was acquired for each patient.

The independent variable was the blood dilution factor i.e. 100%, 50% and 25%. The first dependent variable was the volume (in millilitres, ml) to trigger the alarm of the on-site device, and the second dependent variable was to evaluate whether or not the detection was successful.

The results displayed in Table 1 below illustrates the effectiveness of the on-site device in detecting blood across all conditions, specifically in critical scenarios with lower than normal haematocrit recount and lower than normal concentrations of haemoglobin.

TABLE 1

| Haematocrit Typical Range | Haemoglobin Typical range | Blood Concentration. [Blood:Serum] | | |
|---|---|---|---|---|
| [36, 46] % | [11.5, 15] g/dL | 1:4 | 1:2 | 1:0 |
| 23.6 | 8 | Detected at 0.7 mL | Detected at 0.9 mL | Detected at 0.4 mL |
| 19.5 | 7 | Detected at 1.1 mL | Detected at 1.0 mL | Detected at 0.9 mL |
| 37.9 | 12.7 | Detected at 0.7 mL | Detected at 0.8 mL | Detected at 0.5 mL |

Based on the results of Table 1, it was proven that the on-site device was able to detect haemoglobin at less than 1.2 mL of liquid and in cases where the concentration of blood is diluted.

In the described exemplary embodiments, an on-site device for detecting presence of a liquid from a site may provide effective real-time monitoring for detecting intense external bleeding e.g. after the removal of a central venous catheter (CVC).

In the first few hours following the removal of central venous catheters, severe bleeding from the wound site may occur. These wound sites are pre-emptively heavily bandaged up and placed under blankets. Despite close and regular inspections, catastrophic bleeding may occur and remain undetected, possibly resulting in fatality.

It has been recognised that light-based sensors have been studied in the context of haemorrhages induced by venous needle dislodgement. Optical fibre technology has been proposed to detect venous needle dislodgement through a sensor probe. A light pulse is sent through the fibre and, in presence of blood, the intensity of the returning light pulse is reduced. Other solutions are capable of detecting needle dislodgement by using an attached photo sensor. The sensor is placed under an opaque cover so that it would not be exposed to the ambient light while the needle remains in place. Other studies have proposed to use a sensor pad with a unique electrical pattern overlying the vascular access region to monitor for blood presence. Other techniques include devices that are capable of measuring heart rate or detecting breaks in the electrical circuit composed by the dialysis machine, the patient and the needle.

However, the inventors have recognised that none of the abovementioned studies have been found to provide a sufficiently reliable and cost effective solution to monitoring for haemorrhages. The inventors have recognised that there is a need for an effective real-time monitoring system that is capable of detecting intense external bleeding. Preferably, the monitoring system may alert medical personnel in the event whereby intervention is desired.

The on-site device in the described exemplary embodiments may be applied in the field of biomedical sensing, monitoring and alerting devices and may provide an effective fusion sensing technology capable of detecting and differentiating active bleeding from other fluids at the potential bleeding site with relative low energy consumption and relatively low power consumption The on-site device in the described exemplary embodiments may provide an effective stand-alone electronic platform for constant monitoring of potential bleeding sites for critical re-bleeding, and for alerting medical staff if bleeding is detected. The on-site device in the described exemplary embodiments may employ two techniques. The first is a sensor fusion technique that exploits the unique light absorption spectra of haemoglobin. The second is a moisture sensitive electric circuit that takes advantage of the electrical conductive or capacitance properties of liquids and is able to detect the presence of liquids in the dressings. As a stand-alone platform, the on-site device is capable of providing constant monitoring for extended periods up to 8 hours as compared to regular inspections by medical personnel every 15 or 30 minutes for 2 hours.

The on-site device in the described exemplary embodiments is recognised by the inventors to be different from other blood loss detectors due to its use of two different types of detection techniques, which significantly increases its accuracy and reliability. The on-site device may be capable of detecting presence of moisture and distinguishing between blood and other fluids. Experimental evaluation of the on-site device performed using blood of various concentrations showed a 100% detection accuracy.

The on-site device of described exemplary embodiments may be used to monitor bleeding at catheter extraction points, as well as other wounds caused by trauma, surgery etc. The on-site device may also be customised by changing the sensitivities of the moisture detector, the first optical detector assembly and the second optical detector assembly. For example, the on-site device may be configured to be capable of detecting relatively low amounts of blood (in the order of millilitres, ml), even diluted blood, thus providing an early alert system to medical personnel in the event whereby intervention is desired.

As a stand-alone device, the on-site device of described exemplary embodiments may have relatively low power consumption and may be a power and cost efficient device capable of effectively monitoring potential sites of haemorrhage for external bleeding. In the described exemplary embodiments, the on-site device is configured to detect the presence of haemoglobin (indicating the presence of blood) via a two-stage detection approach. In the first stage, the moisture detector is switched on to detect the presence of liquid. The first optical detector assembly is activated to detect haemoglobin in the second stage only if liquid is present. Therefore, the first optical detector assembly is not required to be constantly in an activated state. This results in efficient use of power and significantly extends battery life.

The on-site device may also be part of a remote warning system via the use of wireless technology. On a larger scale e.g. in a hospital setting, multiple on-site devices may be applied on patients and the on-site devices may use wireless technology such as a Low Energy Bluetooth (BLE) module to trigger a centralised remote warning system or alarm monitoring system which may in turn activate an alarm/alert at a nurse station or an alerting device that is carried by medical personnel. This may effectively notify medical personnel of an urgent event so that the appropriate response and remedy can be administered as soon as possible.

The terms "coupled" or "connected" as used in this description are intended to cover both directly connected or connected through one or more intermediate means, unless otherwise stated.

The terms "on-site" and "in-situ" as used in this description are intended to describe the way a measurement, an observation or an examination of an event is taken at the site/place or in the vicinity of the site/place where the event occurs.

The terms "electromagnetic waves" or "light" as used interchangeably in this description and are intended to cover both visible light in the electromagnetic spectrum and other EM waves outside the visible light spectrum, unless otherwise stated.

The description herein may be, in certain portions, explicitly or implicitly described as algorithms and/or functional operations that operate on data within a computer memory or an electronic circuit. These algorithmic descriptions and/or functional operations are usually used by those skilled in the information/data processing arts for efficient description. An algorithm is generally relating to a self-consistent sequence of steps leading to a desired result. The algorithmic steps can include physical manipulations of physical quantities, such as electrical, magnetic or optical signals capable of being stored, transmitted, transferred, combined, compared, and otherwise manipulated.

Further, unless specifically stated otherwise, and would ordinarily be apparent from the following, a person skilled in the art will appreciate that throughout the present specification, discussions utilizing terms such as "scanning", "calculating", "determining", "replacing", "generating", "initializing", "outputting", and the like, refer to action and processes of an instructing processor/computer system, or similar electronic circuit/device/component, that manipulates/processes and transforms data represented as physical quantities within the described system into other data similarly represented as physical quantities within the system or other information storage, transmission or display devices etc.

The description also discloses relevant device/apparatus for performing the steps of the described methods. Such apparatus may be specifically constructed for the purposes of the methods, or may comprise a general purpose computer/processor or other device selectively activated or reconfigured by a computer program stored in a storage member. The algorithms and displays described herein are not inherently related to any particular computer or other apparatus. It is understood that general purpose devices/machines may be used in accordance with the teachings herein. Alternatively, the construction of a specialized device/apparatus to perform the method steps may be desired.

In addition, it is submitted that the description also implicitly covers a computer program, in that it would be clear that the steps of the methods described herein may be put into effect by computer code. It will be appreciated that a large variety of programming languages and coding can be used to implement the teachings of the description herein. Moreover, the computer program if applicable is not limited to any particular control flow and can use different control flows without departing from the scope of the invention.

Furthermore, one or more of the steps of the computer program if applicable may be performed in parallel and/or sequentially. Such a computer program if applicable may be stored on any computer readable medium. The computer readable medium may include storage devices such as magnetic or optical disks, memory chips, or other storage devices suitable for interfacing with a suitable reader/general purpose computer. In such instances, the computer readable storage medium is non-transitory. Such storage medium also covers all computer-readable media e.g. medium that stores data only for short periods of time and/or only in the presence of power, such as register memory, processor cache and Random Access Memory (RAM) and the like. The computer readable medium may even include a wired medium such as exemplified in the Internet system, or wireless medium such as exemplified in bluetooth technology. The computer program when loaded and executed on a suitable reader effectively results in an apparatus that can implement the steps of the described methods.

The firmware for the on-site device in exemplary embodiments may depend on, but is not limited to, Nordic Semiconductor libraries for the chip NRF51822. Firmware may be written in C programming language and a J-Link CortexM Segger programmer or similar programmer may be used to upload the program into a printed circuit board.

The exemplary embodiments may also be implemented as hardware modules. A module is a functional hardware unit designed for use with other components or modules. For example, a module may be implemented using digital or discrete electronic components, or it can form a portion of an entire electronic circuit such as an Application Specific Integrated Circuit (ASIC). A person skilled in the art will understand that the exemplary embodiments can also be implemented as a combination of hardware and software modules.

Additionally, when describing some embodiments, the disclosure may have disclosed a method and/or process as a particular sequence of steps. However, unless otherwise required, it will be appreciated the method or process should not be limited to the particular sequence of steps disclosed. Other sequences of steps may be possible. The particular order of the steps disclosed herein should not be construed as undue limitations. Unless otherwise required, a method and/or process disclosed herein should not be limited to the steps being carried out in the order written. The sequence of steps may be varied and still remain within the scope of the disclosure.

Further, in the description herein, the word "substantially" whenever used is understood to include, but not restricted to, "entirely" or "completely" and the like. In addition, terms such as "comprising", "comprise", and the like whenever used, are intended to be non-restricting descriptive language in that they broadly include elements/components recited after such terms, in addition to other components not explicitly recited. Further, terms such as "about", "approximately" and the like whenever used, typically means a reasonable variation, for example a variation of +/−5% of the disclosed value, or a variance of 4% of the disclosed value, or a variance of 3% of the disclosed value, a variance of 2% of the disclosed value or a variance of 1% of the disclosed value.

Furthermore, in the description herein, certain values may be disclosed in a range. The values showing the end points of a range are intended to illustrate a preferred range. Whenever a range has been described, it is intended that the range covers and teaches all possible sub-ranges as well as individual numerical values within that range. That is, the end points of a range should not be interpreted as inflexible limitations. For example, a description of a range of 1% to 5% is intended to have specifically disclosed sub-ranges 1% to 2%, 1% to 3%, 1% to 4%, 2% to 3% etc., as well as individually, values within that range such as 1%, 2%, 3%, 4% and 5%. The intention of the above specific disclosure is applicable to any depth/breadth of a range.

In the described exemplary embodiments, the casing (e.g. compare casing 502 of FIG. 5B) functions to house/protect and to shield/isolate internal electronic components of the on-site device from the external environment. The casing is capable of being sterilized by conventional sterilization methods/processes using heat e.g. autoclaving, chemicals e.g. ethylene oxide, and irradiation e.g. gamma rays. Sterilisation allows the on-site device to be reused. Materials which are suitable for making the casing include plastics and polymers such as polycarbonate, polyethylene, polypropylene and polyurethane.

In the described exemplary embodiments, the on-site device has been described to be applied to a central venous catheter removal site. However, the on-site device is not limited as such, and may be used as a generic device to detect active bleeding and differentiate blood from other body fluid. The on-site device may be applied to wounds e.g. sutured site that has undergone surgical operation, and bandaged wounds caused by disease, or trauma.

In the described exemplary embodiments, in the embodiments whereby the on-site device is provided in the form of an integrated bandage where all required electronics are embedded within the bandage, it will be appreciated that the bandage can comprise the various components described in the different exemplary embodiments. It will also be further understood that components providing secondary functions such as wireless communications, remote alarm signal transmission etc. may be omitted to achieve a lower and more economical cost price. In other words, in an exemplary embodiment, an integrated bandage may be provided to have no wireless connection to a system external to the bandage, such as for example, an alarm monitoring remote system. Therefore, the integrated bandage may be configured to be tether-free, i.e. having no external wires for wired or wireless connection to a component or system external to the bandage, such as for example, a power source or a communication system. In an exemplary embodiment, an integrated bandage which is tether-free may be stand-alone and may additionally not interfere with activities of a subject on whom the integrated bandage is applied, such as for example, functional mobility, feeding, bathing, dressing, grooming, toileting etc., of the subject.

It will be appreciated by a person skilled in the art that other variations and/or modifications may be made to the specific embodiments without departing from the scope of the invention as broadly described. The present embodiments are, therefore, to be considered in all respects to be illustrative and not restrictive.

The invention claimed is:

1. An on-site device for detecting presence of a liquid from a site, the device comprising:
    a moisture detector arranged to detect the presence of the liquid based on one or more electrical characteristics of the liquid;
    a first optical detector assembly coupled to the moisture detector, the first optical detector assembly being configured to be activated upon detection of the presence of the liquid by the moisture detector;
    a second optical detector assembly configured to detect the presence of the liquid based on one or more optical characteristics of the liquid, the second optical detector assembly comprising a second electromagnetic wave emitting source and a second electromagnetic wave detector, the second electromagnetic wave emitting source being configured to emit electromagnetic waves with a wavelength of from about 900 nm to about 1000 nm towards a surface of the site, and the second electromagnetic wave detector is configured to detect electromagnetic waves reflected from the surface of the site;
    and wherein upon activation, the first optical detector assembly is configured to detect a substance in the liquid based on one or more optical characteristics of the substance.

2. The on-site device as claimed in claim 1, wherein a sensor portion of the moisture detector is disposed on a base surface of the on-site device for facing towards the site.

3. The on-site device as claimed in claim 2, wherein the sensor portion of the moisture detector is configured to contact the site, and the moisture detector comprises a first electrode and a second electrode arranged to conduct electricity therebetween in the presence of the liquid.

4. The on-site device as claimed in claim 2, wherein the sensor portion of the moisture detector is configured to detect a change in capacitance at the site due to the presence of the liquid at the site.

5. The on-site device as claimed in claim 1, wherein the first optical detector assembly comprises a first electromagnetic wave emitting source and a first electromagnetic wave detector, the first electromagnetic wave emitting source being configured to emit electromagnetic waves with a wavelength of from about 470 nm to about 640 nm towards the surface of the site, and the first electromagnetic wave detector is configured to detect electromagnetic waves reflected from the surface of the site.

6. The on-site device as claimed in claim 5, wherein the first electromagnetic wave detector is configured to detect the substance in the liquid based on an absorption by the substance of the electromagnetic waves.

7. The on-site device as claimed in claim 1, wherein the substance in the liquid is haemoglobin.

8. The on-site device as claimed in claim 1, further comprising an alarm module coupled to the first optical detector assembly, the alarm module configured to trigger an alarm signal upon detection of the presence of the substance in the liquid by the first optical detector assembly.

9. The on-site device as claimed in claim 8, wherein the alarm signal is arranged to activate an alarm of the on-site device, or the alarm signal is arranged to trigger an alert signal to be transmitted to a remote system via wireless transmission from the on-site device, or both.

10. The on-site device as claimed in claim 1, further comprising a casing for housing components of the on-site device, the casing being capable of shielding the first optical detector assembly from external light sources.

11. The on-site device as claimed in claim 10, wherein the casing is arranged to be sterilisable for re-use.

12. The on-site device as claimed in claim 1, wherein the site is a catheter insertion site or a catheter removal site or a site where bleeding potentially occurs.

13. A method for detecting presence of a liquid from a site using an on-site device, the method comprising:
    detecting the presence of the liquid based on one or more electrical characteristics of the liquid using a moisture detector of the on-site device;
    activating a first optical detector assembly of the on-site device upon detection of the presence of the liquid by the moisture detector;
    detecting a substance in the liquid based on one or more optical characteristics of the substance using the first optical detector assembly upon activation; and
    detecting the presence of the liquid based on one or more optical characteristics of the liquid using a second optical detector assembly of the on-site device; emitting electromagnetic waves with a wavelength of from about 900 nm to about 1000 nm towards a surface of the site using a second electromagnetic wave emitting source of the second optical detector assembly; and using a second electromagnetic wave detector of the second optical detector assembly to detect electromagnetic waves reflected from the surface of the site.

14. The method as claimed in claim 13, further comprising contacting the site with a sensor portion of the moisture detector such that a first electrode and a second electrode of the moisture detector is capable of conducting electricity therebetween in the presence of the liquid.

15. The method as claimed in claim 13, further comprising using a sensor portion of the moisture detector to detect a change in capacitance at the site due to the presence of the liquid at the site.

16. The method as claimed in claim 13, wherein the step of detecting a substance in the liquid comprises emitting electromagnetic waves with a wavelength of from about 470 nm to about 640 nm towards the surface of the site using a first electromagnetic wave emitting source of the first optical detector assembly, and using a first electromagnetic wave detector of the first optical detector assembly to detect electromagnetic waves reflected from the surface of the site.

17. The method as claimed in claim 16, wherein the step of using the first electromagnetic wave detector of the first optical detector assembly to detect electromagnetic waves reflected from the surface of the site comprises determining an absorption by the substance of the electromagnetic waves.

18. The method as claimed in claim 13, wherein the substance in the liquid is haemoglobin.

19. The method as claimed in claim 13, further comprising triggering an alarm signal upon detection of the presence of the substance in the liquid by the first optical detector assembly, the triggering using an alarm module coupled to the first optical detector assembly.

20. The method as claimed in claim 19, further comprising activating an alarm of the on-site device using the alarm signal, or triggering an alert signal to be transmitted to a remote system via wireless transmission using the alarm signal, or both.

21. The method as claimed in claim 13, further comprising shielding the first optical detector assembly from external light sources using a casing, the casing suitable for housing components of the on-site device.

22. The method as claimed in claim 13, wherein the site is a catheter insertion site or a catheter removal site or a site where bleeding potentially occurs.

23. A bandage for detecting presence of a liquid from a site, the bandage comprising:
- an on-site device for detecting presence of a liquid from a site, the device comprising:
- a moisture detector arranged to detect the presence of the liquid based on one or more electrical characteristics of the liquid;
- a first optical detector assembly coupled to the moisture detector, the first optical detector assembly being configured to be activated upon detection of the presence of the liquid by the moisture detector;
- a second optical detector assembly configured to detect the presence of the liquid based on one or more optical characteristics of the liquid, the second optical detector assembly comprising a second electromagnetic wave emitting source and a second electromagnetic wave detector, the second electromagnetic wave emitting source being configured to emit electromagnetic waves with a wavelength of from about 900 nm to about 1000 nm towards a surface of the site, and the second electromagnetic wave detector is configured to detect electromagnetic waves reflected from the surface of the site;
- and wherein upon activation, the first optical detector assembly is configured to detect a substance in the liquid based on one or more optical characteristics of the substance;
- a primary dressing capable of covering the site;
- a secondary dressing configured to cover the primary dressing and functioning as an external surface of the bandage;
- wherein the on-site device is provided between the primary dressing and the secondary dressing and is arranged to be positioned in the vicinity of the site with the primary dressing.

* * * * *